United States Patent [19]

Chen et al.

[11] Patent Number: 5,693,666

[45] Date of Patent: Dec. 2, 1997

[54] 6,7-MODIFIED PACLITAXELS

[75] Inventors: Shu-Hui Chen, Hamden; Vittorio Farina, West Hartford; Gregory Roth, Cheshire; John Kadow, Wallingford, all of Conn.

[73] Assignee: Bristol-Myers Squibb Company, New York, N.Y.

[21] Appl. No.: 582,322

[22] Filed: Jan. 3, 1996

Related U.S. Application Data

[60] Continuation of Ser. No. 314,035, Sep. 28, 1994, abandoned, which is a division of Ser. No. 128,619, Sep. 28, 1993, Pat. No. 5,380,751, which is a continuation-in-part of Ser. No. 985,761, Dec. 4, 1992, abandoned.

[51] Int. Cl.$^6$ .................. A61K 31/335; C07D 305/14
[52] U.S. Cl. ................... 514/444; 514/471; 549/60; 549/473
[58] Field of Search .................. 549/60, 473; 514/444, 514/471

[56] References Cited

U.S. PATENT DOCUMENTS

| | | |
|---|---|---|
| 4,814,470 | 3/1989 | Colin et al. |
| 4,876,399 | 10/1989 | Holton et al. |
| 5,015,744 | 5/1991 | Holton . |
| 5,136,060 | 8/1992 | Holton . |
| 5,175,315 | 12/1992 | Holton . |
| 5,227,400 | 7/1993 | Holton et al. |
| 5,229,526 | 7/1993 | Holton . |
| 5,243,045 | 9/1993 | Holton et al. |
| 5,248,796 | 9/1993 | Chen et al. |
| 5,283,253 | 2/1994 | Holton et al. |
| 5,284,864 | 2/1994 | Holton et al. |
| 5,284,865 | 2/1994 | Holton et al. |
| 5,294,637 | 3/1994 | Chen et al. |
| 5,395,850 | 3/1995 | Roth ............................. 514/471 |
| 5,430,160 | 7/1995 | Holton . |

FOREIGN PATENT DOCUMENTS

| | | |
|---|---|---|
| 400971A2 | 12/1990 | European Pat. Off. |
| 522958A1 | 1/1993 | European Pat. Off. |
| 524093A1 | 1/1993 | European Pat. Off. |
| 534709A1 | 3/1993 | European Pat. Off. |
| 558959A1 | 9/1993 | European Pat. Off. |
| WO 9209589 | 6/1992 | WIPO . |
| WO 9306079 | 4/1993 | WIPO . |
| WO 9306093 | 4/1993 | WIPO . |
| WO 9306094 | 4/1993 | WIPO . |
| WO 9429288 | 12/1994 | WIPO . |

OTHER PUBLICATIONS

Gunda I. Georg et al, "Novel Biologically Active Taxol Analogues: Baccatin III 13-(N-(p-Chlorobenzoyl)-(2'R, 3'S)-3'-phenylisoserinate) and Baccatin III 13-(N-benzoyl-(2'R, 3'S)-3'-(p-chlorophenyl)isoserinate)," *Bioorganic and Medicinal Chemistry Letters*, vol. 2, No. 4, pp. 295-298, 1992.

Gunda I. Georg et al., "Semisynthesis and Biological Activity of Taxol Analogues: Baccatin III 13-(N-benzoyl-(2'R, 3'S)-3'-(p-tolyl)isoserinate), Baccatin III 13-(N-(p-toluoyl)-(2'R,3'S)-3'-(phenylisoserinate), Baccatin III 13-(N-benzoyl-(2'R, 3'S)-3'-(p-trifluoromethylphenyl)isoserinate), and Baccatin III 13-(N-(p-trifluoromethylbenzoyl)-(2'R, 3'S)-3'-phenylisoserinate)," *Bioorganic and Medicinal Chemistry Letters*, vol. 2, No. 12, pp. 1751-1754, 1992.

Gunda I. Georg et al., "Synthesis of Biologically Active Taxol Analogues with Modified Phenylisoserine Side Chains," *Journal of Medicinal Chemistry*, vol. 35, pp. 4230-4237, 1992.

F. Gueritte-Voegelein et al., "Relationships between the Structure of Taxol Analogues and Their Antimitotic Activity," *Journal of Medicinal Chemistry*, 34, pp. 992-998, 1991.

D.G.I. Kingston, et al, "The Chemistry of Taxol, A Clinically Useful Anticancer Agent", *Journal of Natural Products*, 53, No. 1, pp. 1-12, 1990.

N.F. Magri and D.G.I. Kingston, "Modified Taxols. 2.1 Oxidation Products of Taxol", *J. Org. Chem.*, 51, pp. 797-802, 1986.

N.F. Magri and D.G.I. Kingston, "Modified Taxols, 4. Synthesis and Biological Activity of Taxols Modified in the Side Chain", *Journal of Natural Products*, 51, No. 2, pp. 298-306, 1988.

Iwao Ojima et al., "Efficient and Practical Asymmetric Synthesis of the Taxol C-13 Side Chain, N-Benzoyl-(2 R,3 S)-3-phenylisoserine, and Its Analogues via Chiral 3-Hydroxy-4-aryl-β-lactams through Chiral Ester Enolate-Imine Cyclocondensation," *Journal of Organic Chemistry*, vol. 56, pp. 1681-1683, 1991.

Iwao Ojima et al., "New and Efficient Approaches to the Semisynthesis of Taxol and Its C-13 Side Chain Analogs by Means of β-Lactam Synthon Method," *Tetrahedron*, vol. 48, No. 34, pp. 6985-7012, 1992.

(List continued on next page.)

*Primary Examiner*—Joseph McKane
*Attorney, Agent, or Firm*—Samuel J. DuBoff; William T. Han

[57] ABSTRACT

The present invention provides paclitaxel derivatives of formula I

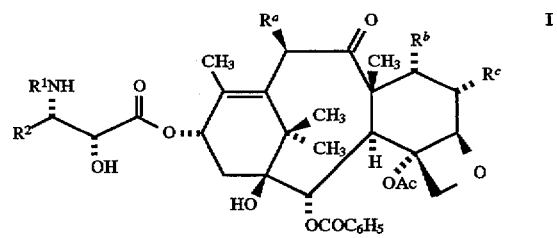

and pharmaceutical compositions.

7 Claims, No Drawings

OTHER PUBLICATIONS

Iwao Ojima et al., "New and Efficient Routes to Norstatine and Its Analogs with High Enantiomeric Purity by β–Lactam Synthon Method," *Tetrahedron Letters*, vol. 33, No. 39, pp. 5737–5740, 1992.

C. S. Swindell et al, "Biologically Active Taxol Analogues with Deleted A–Ring Side Chain Substituents and Variable C–2' Configurations," *Journal of Medicinal Chemistry*, 34, pp. 1176–1184, 1991.

M. A. Tius, et al, "Halogenated Cannabinoid Synthesis," *Tetrahedron*, vol. 49, No. 16, pp. 3291–3304, 1993.

Michel Biollaz and Jaroslav Kalvoda, "Reactions of Steroids with Dialkylaminosulfur Trifluorides. I. 11β–Hydroxysteroids.", *Helvetica Chimica Acta*, vol. 60, Fasc. 8, No. 263, pp. 2703–2710, 1977.

An abstract from Stony Brook Symposium on Taxol and Taxotere New Hope for Breast Cancer, May 14 and 15, 1993, G. N. Chmurny, et al, "Purification and 2D NMR Structure Determination of 6–α Hydroxtaxol, a Major Human Metabolite of Taxol," pp. 48–49.

6,7-MODIFIED PACLITAXELS

REFERENCE TO RELATED APPLICATIONS

This application is a continuation of U.S. Ser. No. 08/314,035 filed Sep. 28, 1994, now abandoned, which is a divisional of U.S. Ser. No. 08/128,619, filed Sep. 28, 1993, U.S. Pat. No. 5,380,751 issued Jan. 10, 1995, which is a continuation-in-part of U.S. Ser. No. 07/985,761 filed Dec. 4, 1992, now abandoned.

FIELD OF INVENTION

The present invention provides compounds having antitumor activities.

BACKGROUND OF INVENTION

TAXOL® (paclitaxel) was first isolated from the stem bark of Western Yew, *Taxus brevifolia* Nut. (Taxaceae) and has the following structure (with the (C) 2'-, 6-, 7-, and 13th-positions indicated):

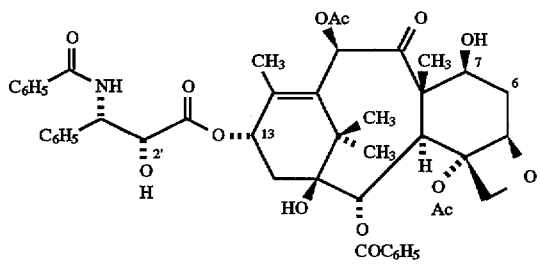

It was recently approved for the treatment of ovarian cancer; and studies involving breast, colon, and lung cancers have shown promising results. See: D. K., and Donebower, R. C. Ann. Int. Med., 1989, 111, p 273.

Paclitaxel is unique among antimitotic drugs in that it promotes the assembly of stable microtubules from tubulin even under otherwise unfavorable conditions. The drug binds to microtubules, stabilizing them from depolymerization, thus disrupting the tubulin-microtubule equilibrium and consequently inhibiting mitosis. The mechanism of action, toxicology, clinical efficacy, etc. of paclitaxel are reviewed in a number of articles, such as in the article by Rowinsky et al. in Taxol: *A Novel Investigational Antimicrotubule Agent*, J. Natl. Cancer Inst., 82: pp 1247–1259 (1990).

Since the discovery of its significant effectiveness in cancer treatment, many laboratories have launched programs to design paclitaxel analogues in search of better pharmacological profiles. Out of such programs, for example, was the discovery of Taxotere® of the formula

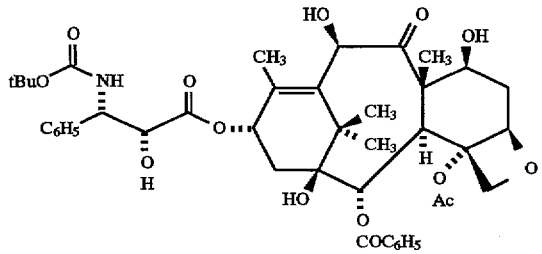

See, *Biologically Active Taxol Analogues with Deleted A-Ring Side Chain Substitutents and Variable C-2' Configurations*, J. Med. Chem., 34, pp 1176–1184 (1991); *Relationships between the Structure of Taxol Analogues and Their Antimitotic Activity*, J. Med. Chem., 34, pp 992–998 (1991).

The present invention relates to structurally novel paclitaxel derivatives with antitumor activities.

SUMMARY OF INVENTION

The present invention provides paclitaxel derivatives of formula I

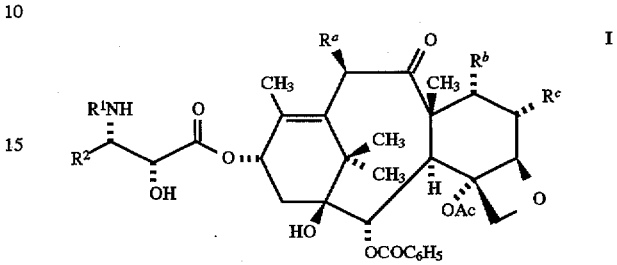

in which $R^1$ is —$COR^Z$ in which $R^Z$ is RO— or R;

$R^2$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, phenyl, or heteroaryl, and furthermore $R^x$ can be optionally substituted with one to three same or different $C_{1-6}$ alkyl, $C_{1-6}$ alkoxy, halogen or —$CF_3$ groups;

$R^a$ is —OCOR, H, OH, —OR, —$OSO_2R$, —$OCONR^oR$, —OCONHR, —OCOO$(CH_2)_tR$, or —OCOOR;

$R^b$ and $R^c$ are both hydroxy or together form a bond with the carbon atoms to which they are attached; and R and $R^o$ are independently $C_{1-6}$ alkyl, $C_{2-6}$ alkenyl, $C_{3-6}$ cycloalkyl, $C_{2-6}$ alkynyl, or phenyl, optionally substituted with one to three same or different $C_{1-6}$ alkyl, $C_{1-6}$ alkoxy, halogen or —$CF_3$ groups.

Also provided by this invention are pharmaceutical formulations (compositions) and a method of treating mammalian tumors with a compound of formula I.

DETAILED DESCRIPTION OF INVENTION

The present invention provides paclitaxel derivatives of formula I

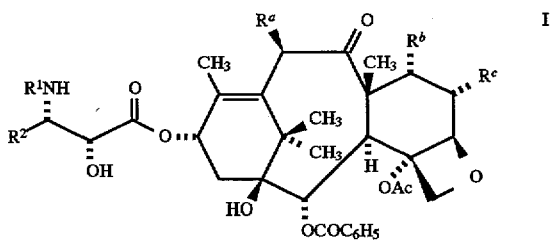

in which $R^1$ is —$COR^Z$ in which $R^Z$ is RO— or R;

$R^2$ is $C_{1-6}$ alkyl, $C_{2-6}$ alkenyl, $C_{2-6}$ alkynyl, $C_{3-6}$ cycloalkyl, or a radical of the formula —W—$R^x$ in which W is a bond, $C_{2-6}$ alkenediyl, or —$(CH_2)_t$—, in which t is one to six; and $R^x$ is naphthyl, phenyl, or heteroaryl, and furthermore $R^x$ can be optionally substituted with one to three same or different $C_{1-6}$ alkyl, $C_{1-6}$ alkoxy, halogen or —$CF_3$ groups;

$R^a$ is —OCOR, H, OH, —OR, —$OSO_2R$, —$OCONR^oR$, —OCONHR, —OCOO$(CH_2)_tR$, or —OCOOR;

$R^b$ and $R^c$ are both hydroxy or together form a bond with the carbon atoms to which they are attached; and R and R° are independently $C_{1-6}$ alkyl, $C_{2-6}$ alkenyl, $C_{3-6}$ cycloalkyl, $C_{2-6}$ alkynyl, or phenyl, optionally substituted with one to three same or different $C_{1-6}$ alkyl, $C_{1-6}$ alkoxy, halogen or —$CF_3$ groups.

In the instant application, the numbers in subscript after the symbol "C" define the number of carbon atoms a particular group can contain. For example, $C_{1-6}$ alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl, or the like alkyl groups; $C_{2-6}$ alkenyl refers to straight or branched alkenyl groups such as vinyl, allyl, 1-propenyl, isopropenyl, 1-butenyl, 2-butenyl, 3-butenyl, methallyl, 1,1-dimethylallyl, 1-hexenyl, 2-hexenyl, or the like groups; $C_{3-6}$ cycloalkyl refers to cyclopropyl, cyclobutyl, cyclopentyl, or cyclohexyl; $C_{2-6}$ alkynyl refers to straight or branched alkynyl groups such as ethynyl, propargyl (2-propynyl), 1-propynyl, 2-butynyl, 3-butynyl, 1-hexynyl, 4-methyl-2-pentynyl, and the like groups; $C_{2-6}$ alkenediyl refers to groups such as ethylene-1,2-diyl (vinylene), 2-methyl-2-butene-1,4-diyl, 2-hexene-1,6-diyl, and the like groups; $C_{1-6}$ alkyloxy (alkoxy) refers to straight or branched alkyloxy groups such methoxy, ethoxy, n-propoxy, i-propoxy, n-butoxy, t-butoxy (t-butyloxy), n-pentyloxy, n-hexytoxy, or 3-methylpentyloxy, to name a few; heteroaryl refers to a five-membered aromatic ring containing at least one heteroatom selected from sulfur, oxygen or nitrogen, but up to 1 sulfur, 1 oxygen or 4 nitrogen atoms; heteroaryl also refers to a six-membered aromatic ring containing from 1 to 4 nitrogen atoms; and halogen refers to fluorine, chlorine, bromine, or iodine. Examples of heteroaryl include thienyl, furyl, pyrrolyl, imidazolyl, pyrazolyl, thiazotyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings. Azetidinone refers to azetidin-2-one. In the instant application all symbols once defined retain the same meaning until they are redefined.

The synthesis of a compound of formula I can be accomplished by a wide variety of methods. The synthetic methods, descriptions and specific examples that follow are only intended for the purpose of illustration, and are not to be construed as limiting in any manner ways to make compounds of the present invention by any other methods. The methods disclosed herein can be readily modified and/or adapted to make additional compounds of formula I not specifically disclosed.

In one embodiment, compound of formula Ia can be made by a process of Scheme I. In th Scheme, when compound of formula IIa is treated with DAST, compound of formula IIIa can be obtained. The DAST reaction can be conducted in a wide variety of solvents, including methylene chloride, tetrahydrofuran (THF), diethyl ether, toluene, and any combination thereof. In addition to compound IIIa, compounds of formula IVa and Va may be obtained as side products in the DAST reaction. It has been observed that the highest ratio of compound IIIa to compound IVa or a is obtained when the reaction is run in a mixture of THF and diethyl ether. Upon removal of Cbz group from compound of formula IIIa, compound of formula Ia is obtained.

In a more general embodiment of Scheme II, when compound of formula Ia is treated with an ester reducing agent such as tetrabutylammonium borohydride, C-13 side chain is eductively cleaved to afford compound of formula VIa. Compound of formula VIa can be coupled with an azetidinone of formula VII in a substantially same manner as in Step (a) of Scheme IV (vide infra) to afford a compound of formula VIII. Upon removal of hydroxy protecting group $R^3$, a compound of formula $I^1$ can be obtained.

As used herein, hydroxy protecting groups are moieties which can be employed to block or protect the hydroxy function and they are well known to those skilled in the art. Preferably, said groups are those which can be removed by methods which result in no appreciable destruction to the remaining portion of the molecule. Examples of such readily removable hydroxy protecting groups include chloroacetyl, methoxymethyl, 2,2,2-trichloroethyoxymethyl, 2,2,2-trichloroethyloxycarbonyl, tetrahydropyranyl, tetrahydrofuranyl, t-butyl, benzyl, p-nitrobenzyl, p-methoxybenzyl, diphenylmethyl, tri$C_{1-6}$alkylsilyl, triphenylsilyl, 1-ethoxyethyl, and the like. Preferred protecting groups for the 2'-hydroxy group of paclitaxel and a derivative thereof are 1-ethoxyethyl, triethylsilyl, 2,2,2-trichloroethyloxycarbonyl and benzyloxycarbonyl; even more preferred group is benzyloxycarbonyl, which can be removed conveniently by catalytic hydrogenolysis. Other suitable protecting groups which can be used are found in Chapter 2 of "Protecting Groups in Organic Synthesis", Second Ed., by Theodora W. Greene and Peter G. M. Wuts (1991, John Wiley & Sons); the disclosure thereof is herein incorporated by reference.

In another general embodiment, a compound of formula II can be reacted with DAST as in Step (a) of Scheme I to afford a compound of formula III. Scheme III. As used herein, $R^j$ is —OCOR, H, —OR, —$OR^3$, —$OSO_2R$, —OCONR°R, —OCONHR, —$OCOO(CH_2)_xR$, or —OCOOR. Upon removal of hydroxy protecting group(s) $R^3$, a compound of formula $I^2$ is obtained.

Many of the compounds represented by formula II are already known in the art or can be readily obtained using known processes, with or without minor modifications. For example, a compound of formula II in which $R^j$ is hydrogen can be made by the general methods described in PCT application WO 93/06093 published Apr. 1, 1993, which is herein incorporated by reference in its entirety.

As a further illustration, compounds of formula II can be readily made by the process of Scheme IV. In Step (a) of the scheme, azetidinone VII is reacted with a compound of formula X (a baccatin III derivative), in which $R^4$ is a hydroxy protecting group. The general class of azetidinones of formula VII are well known. Their syntheses or syntheses of their precursors have been reported such as by Holton in European Patent Application 0,400,971 A2 published on Dec. 5, 1990; by Holton in European Patent Applications 0,534,709 A1, 0,534,708 A1, and 0,534,707 A1, all three published on Mar. 31, 1993; also by Holton in PCT application WO 93/06079 published on Apr. 1, 1993; by Ojima et al. in *Tetrahedron*, 48, No. 34, pp 6985–7012 (1992); *Journal of Organic Chemistry*, 56, pp 1681–1683 (1991); and *Tetrahedron Letters*, 33, No. 39, pp 5737–5740 (1992); by Brieva et al. in *J. Org. Chem.*, 58, pp 1068–1075; by Palomo et al. in *Tetrahedron Letters*, 31, No. 44, pp 6429–6432 (1990); European Application 552,041 published on Jul. 21, 1993; and our copending U.S. application Ser. No. 092,170 filed on Jul. 14, 1993: all twelve disclosures are herein incorporated by reference in their entirety. The methods that can be easily adapted to variations in order to produce other azetidinones within the scope of formula VII, but not specifically disclosed herein or in the above twelve references or reported elsewhere, will be obvious to anyone skilled in the art.

European Patent Applications 0,400,971 A2 0,534,709 A1, 0,534,708 A1, and 0,534,707 A1; and *Tetrahedron*, 48, No. 34, pp 6985–7012 (1992) and Tetrahedron Letters, 34, No. 26, pp 4149–4152 (1993) also describe processes whereby the class of azetidinones of formula VII are reacted with (C)13-hydroxy group of baccatin III derivatives or metal alkoxide thereof to afford paclitaxel analogues with a variety of (C)13-side chains. In Step (a) of Scheme IV, it is advantageous to convert the hydroxy group on the (C)13-carbon into a metal alkoxide before the coupling. The metal cation of said metal alkoxide is preferably selected from Group Ia or IIa metals. The formation of a desired metal alkoxide may be done by reacting a compound of formula II with a strong metal base, such as lithium diisopropylamide, $C_{1-6}$ alkyllithium, lithium bis(trimethylsilyl)amide, phenyllithium, sodium hydride, potassium hydride, lithium hydride, or the like base. For example when lithium alkoxide is desired, a compound of formula II may be reacted with n-butyllithium in an inert solvent such as tetrahydrofuran.

A compound of formula X is either known in the art or can be readily obtained by known processes, with or without minor modifications. For example, a compound of formula X in which $R^4$ is triethylsilyl and $R^j$ is acetyloxy is reported in U.S. Pat. No. 4,924,011, issued to Denis et al on May 8, 1990. Moreover, as in Scheme V, when a compound of formula IX is reacted with RL, RC(=O)L, R(CH$_2$)$_r$OC(=O)L, ROC(=O)L, LSO$_2$R, LCONR°R, LCONHR, O=C=N—R or an anhydride derivative thereof, in which L is a typical leaving group such as chloro, bromo, mesyl, trifluoromethanesulfonyl, or tosyl, a compound of formula $X^1$, which is within the scope of formula X, can be obtained. As used herein $R^m$ is —OR, —OCOR, —OSO$_2$R —OCONR°R, —OCONHR, —OCOO(CH$_2$)$_r$R, or —OCOOR. A base is normally required in the process of Scheme V to initially deprotonate a proton from C-10 hydroxy group. A particularly useful base for Step (a) is a strong base such as $C_{1-6}$ alkyllithium, lithium bis(trimethylsily)amide, or the like base used in about 1.1 equivalent amount. The deprotonation by base is preferably conducted in an aprotic solvent, such as tetrahydrofuran, at low temperature, usually in the range from −40° to 0° C. The synthesis of a compound of formula IX in which $R^4$ is triethylsilyl is described in U.S. Pat. No. 4,924,011, issued to Denis et al. on May 8, 1990. Compounds of formula IX in which $R^4$ is other than trialkylsilyl are either known or can be readily made by processes obvious to any person skilled in the art.

As illustrated in Scheme VI, a compound of formula $I^3$ can be made by reacting a compound of formula XIII with osmium tetraoxide and 4-methylmorpholine-N-oxide (NMO) followed by the removal of hydroxy protecting group $R^3$ from a compound of formula XII.

SCHEME I

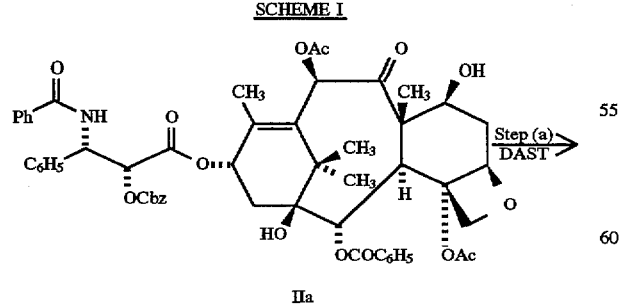

IIa

-continued
SCHEME I

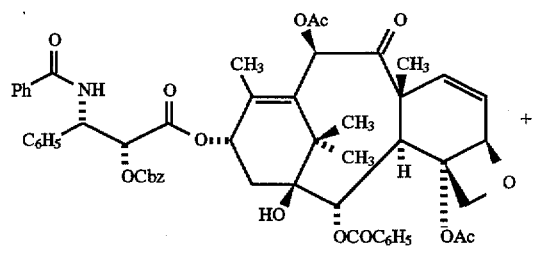

IIIa

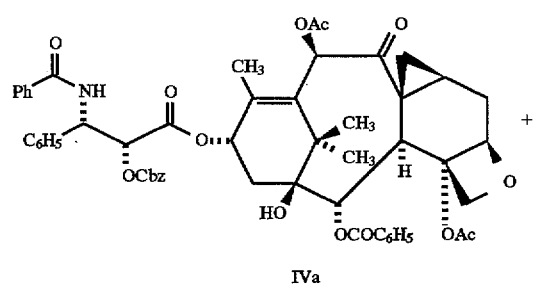

IVa

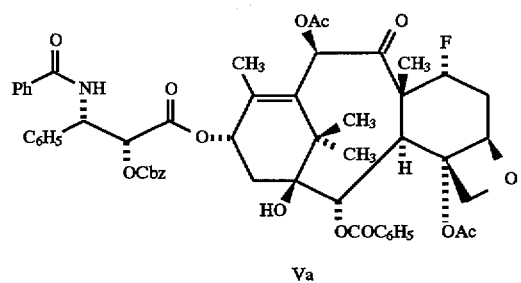

Va

IIIa Step (b)→

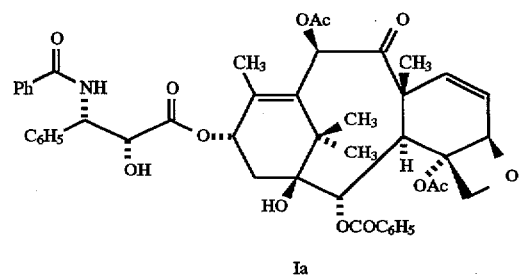

Ia

SCHEME II
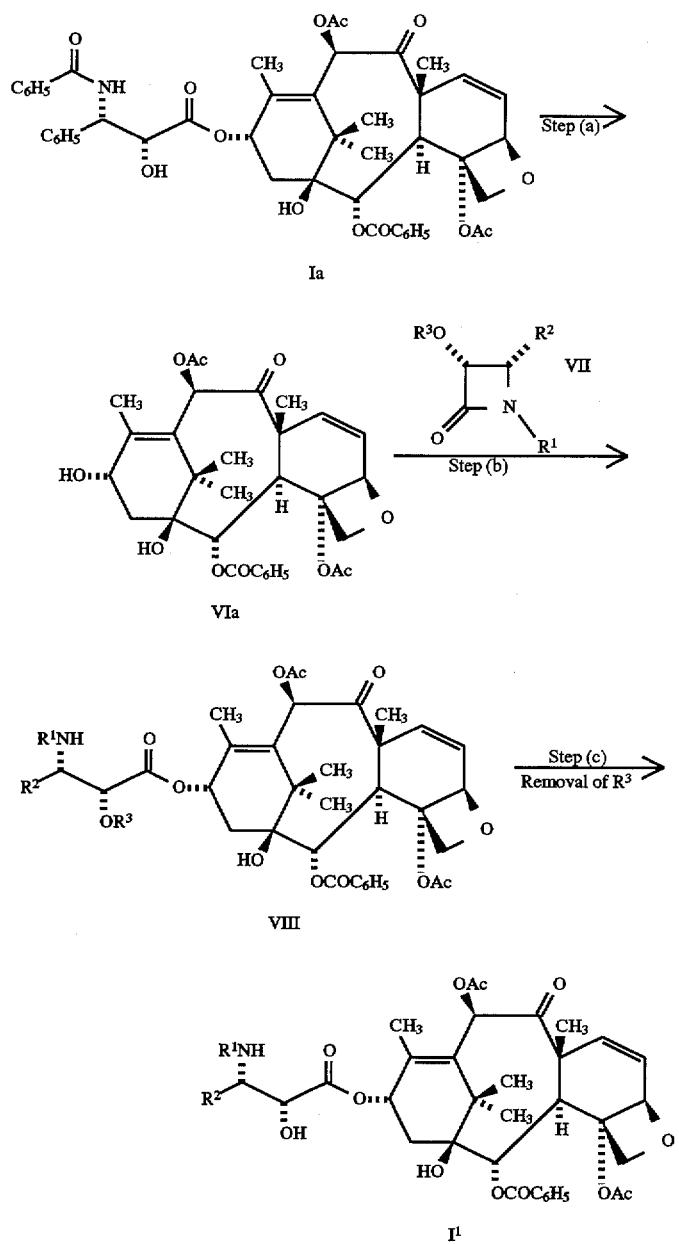
SCHEME III
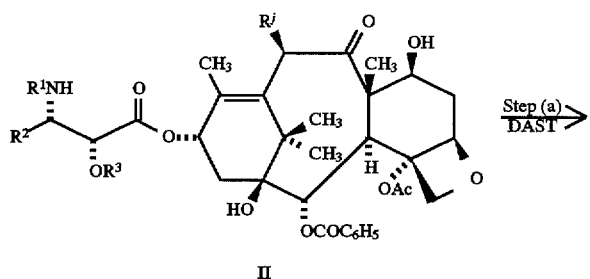

-continued
SCHEME III
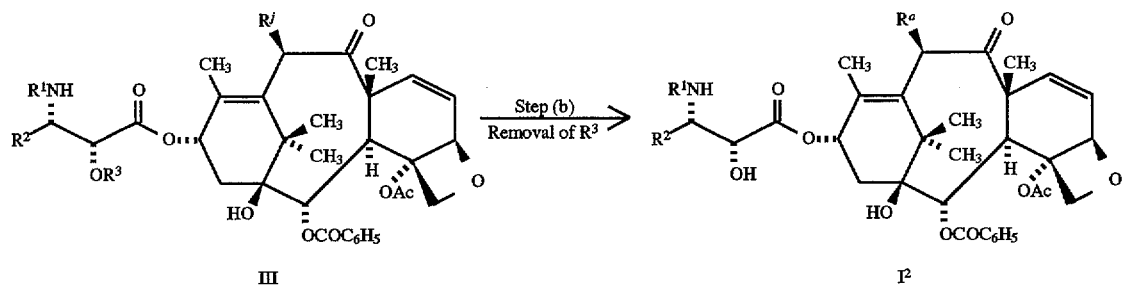
SCHEME IV
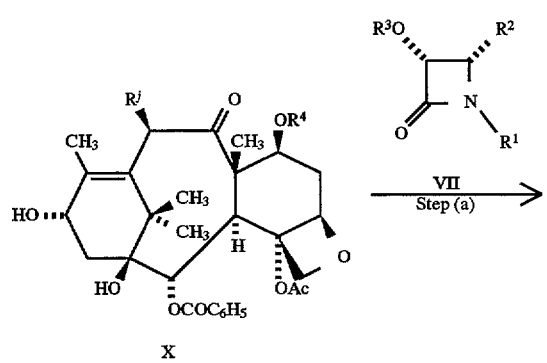
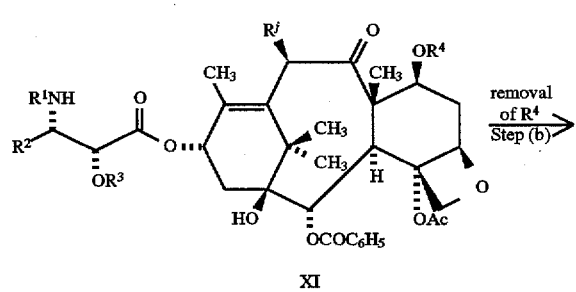
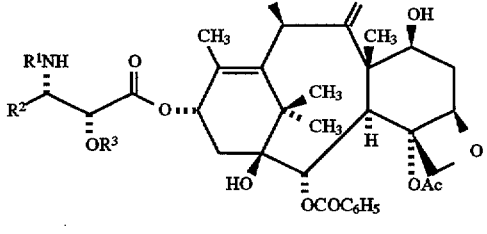
Scheme V
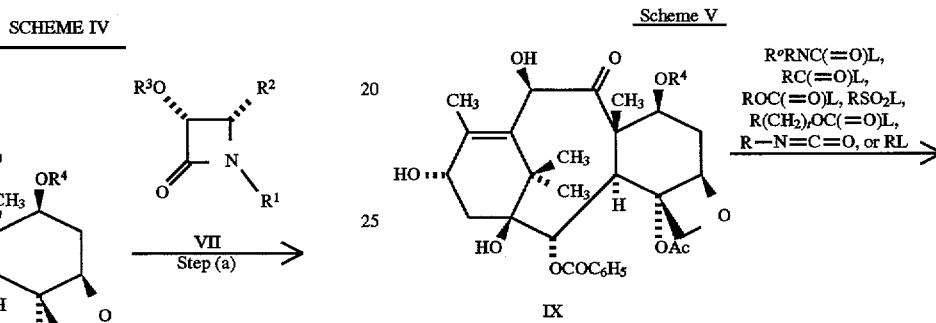
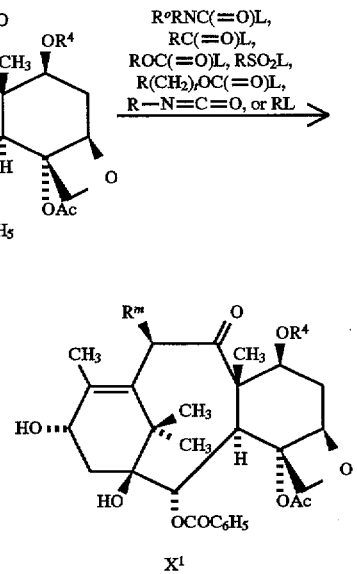
SCHEME VI
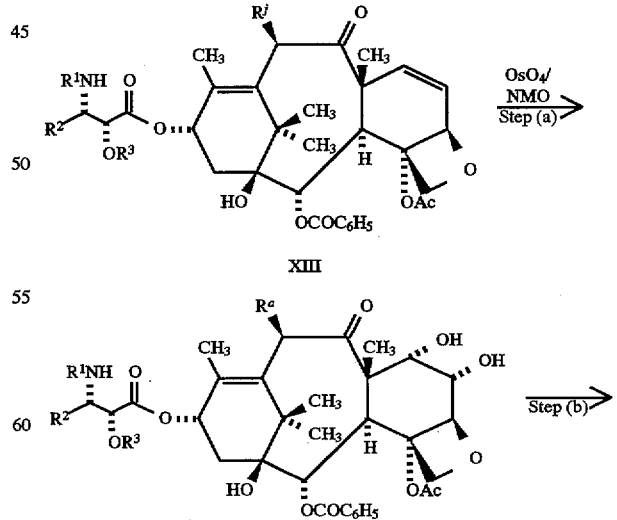

-continued
SCHEME VI

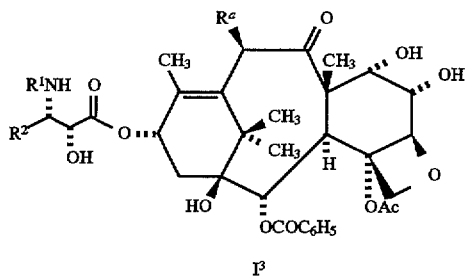

P³

DESCRIPTION OF SPECIFIC EMBODIMENTS

The structural formulae as drawn in the instant application are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

The specific examples which follow illustrate the synthesis of representative compounds of the instant invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

Celite is a registered trademark of the Johns-Manville Products Corporation for diatomaceous earth.

The abbreviations used herein are conventional abbreviations widely employed in the art. Some of which are:
MS: mass spectrometry
HRMS: high resolution mass spectrometry
DAST: diethylaminosulfur trifluoride
Ac: acetyl
Ph: phenyl
Ar: aryl
DCI: desorption chemical ionization
Y: yield
v/v: volume/volume
FAB: fast atom bombardment
NOBA: m-nitrobenzylalcohol min: minute(s)
h: hour(s)
tBu: tertiarybutyl
Cbz: benzyloxycarbonyl
Bz: benzoyl
TES: triethylsilyl

EXAMPLE 1

2'-O-[Benzyloxycarbonyl)paclitaxel (IIa)

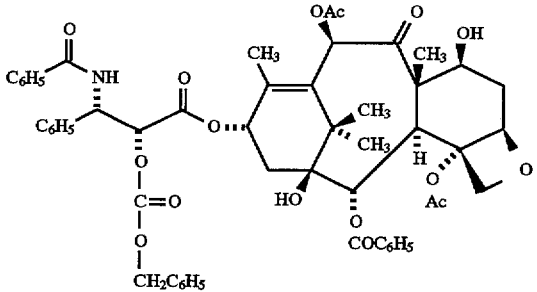

To a stirred, room temperature solution of paclitaxel (150 mg, 0.176 mmol) and N,N-diisopropylethylamine (93 μL, 0.534 mmol, 3 eq.) in anhydrous $CH_2Cl_2$ (4 mL) was added benzyl chloroformate (75 μL, 0.525 mmol, 3 eq.) at room temperature. The reaction mixture was stirred at room temperature for 3 h. The reaction mixture was concentrated to 2 mL in volume and the product was purified on a silica gel column, using 1:1 of EtOAc/hexanes as eluent, to obtain 150 mg (0.152 mmol, Y: 86%) of the title compound, IIa, as a white powder; mp, 140°–150° C. (decomposition); $[\alpha]_D^{20}$–53.5° (c=0.2, 95% EtOH); $^1$H-NMR (300 MHZ, acetone-$d_6$) δ ppm: 1.18 (3H, s, 17-$H_3$), 1.92 (3H, s, 16-$H_3$), 1.66 (3H, s, 19-$H_3$), 1.96 (3H, s, 18-$H_3$), 2.16 (3H, s, 10-OAc), 2.5 (3H, s, 4-OAc), 3.53 (1H, d, J=5.89 Hz, 7-OH, exchanged with $D_2O$), 3.85 (1H, d, J=7.19 Hz, 3-H), 3.9 (1H, s, 1-OH, exchanged with $D_2O$), 4.17 (2H, ABq, 20-$H_2$), 4.25 (1H, m, 7-H), 4.97 (1H, d, J=9.56 Hz, 5-H), 5.19 (2H, ABq, O$CH_2C_6H_5$), 5.54 (1H, d, J=5.5 Hz, 2'-H), 5.68 (1H, d, J=7.13 Hz, 2-H), 6.01 (1H, dd, J=5.5, 9.05 Hz, 3'-H), 6.17 (1H, bt, J=9.0 Hz, 13-H), 6.42 (1H, s, 10-H), 7.28–7.69 (16H, m), 7.87 (2H, "d", J=8 Hz, 3'-NHCOPh), 8.14 (2H, "d", J=8 Hz, 2-CO$_2$Ph), 8.55 (1H, d, J=9.06 Hz, N$H$, exchanged with $D_2O$); MS (FAB-NOBA/NaI+KI) m/e: 988 (M+H)$^+$, 1010 (M+Na)$^+$, 1026 (M+K)$^+$; IR (KBr) ν max: 3448, 1748 (C=O), 1726 (CONH), 1250 (C—O) $cm^{-1}$; UV (MeOH:$H_2O$, 1:1) λ max: 198 (ε 7.3×10$^4$), 230 nm (ε 2.7×10$^4$); HRMS calcd for $C_{55}H_{58}NO_{16}$ (MH$^+$): 988.3756, found: 988.3766.

Anal. calcd for $C_{55}H_{57}NO_{16} \cdot H_2O$: C, 65.67; H, 5.92; N, 1.40. Found: C, 65.99; H, 5.64; N, 1.33.

EXAMPLE 2

2'-O-Benzyloxycarbonyl-6,7-dehydropaclitaxel (IIIa).

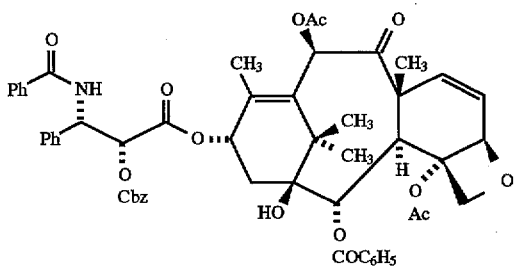

2'-O-(Benzyloxycarbonyl)paclitaxel (IIa) (514 mg, 0.521 mmol) was dissolved in THF (3 mL) and $Et_2O$ (6 mL). This solution was cooled to –78° C. and DAST (0.134 mL, 1.040 mmol) was added dropwise. The reaction was stirred at –78° C. for 3 h, and then left at room temperature overnight. When the reaction was complete, the solvent was partially removed in vacuo, and the residue was chromatographed with 30–40% EtOAc in hexane to afford 73 mg (Y: 14.5%) of the desired product; $^1$H-NMR ($CDCl_3$, 300 MHz) δ ppm: 8.15 (d, J=7.1 Hz, 2H), 7.71 (d, J=7.1 Hz, 2H) 7.63–7.24 (m, 16H) 6.90 (d, exch, J=9.3 Hz, 1H) 6.25 (bt, 1H) 6.21 (s, 1H) 6.05 (dd, $J_1$=9.9 Hz, $J_2$=5.6 Hz, 1H) 5.96 (d, $J_1$=9.9 Hz, $J_2$=2.7 Hz, 1H) 5.86–5.82 (m, 2H) 5.42 (d, J=2.5 Hz, 1H) 5.18–5.09 (m, 3H) 4.37 (AB q, J=8.2 Hz, 2H) 4.00 (d, J=6.6 Hz, 1H) 2.48–1.12 (m, 21H, including s at 2.44, 3H; 2.18, 3H; 1.86, 3H; 1.84, 3H; 1.23 3H; 1.13, 3H); $^{13}$C-NMR ($CDCl_3$, 75 MHz) δ ppm: 205.5, 169.5, 169.1, 167.8, 167.1, 167.0, 154.1, 141.9, 139.9, 136.8, 134.3, 133.7, 133.5, 132.0, 130.2, 129.2, 129.1, 128.9, 128.7, 128.4, 127.2, 126.6, 126.2, 81.2, 81.1, 78.8, 76.9, 76.3, 75.9, 75.7, 71.9, 70.7, 55.4, 52.7, 43.1, 41.4, 35.8, 26.4, 22.8, 22.1, 21.0, 20.8, 20.5, 14.5.

EXAMPLE 3

6,7-Dehydropaclitaxel (Ia)

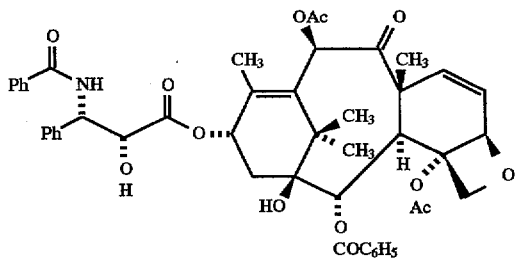

2'-O-Benzyloxycarbonyl-6,7-dehydropaclitaxel (IIIa) (19.6 mg, 0.020 mmol) was dissolved in EtOAc (0.5 mL). A catalytic amount of Pd/C (6.4 mg, 10%, 0.006 mmol) was added to the above solution, and the reaction was subjected to hydrogenolysis at atmospheric pressure. After 4 h, the mixture was filtered, the filtrate evaporated and the crude product was purified by chromatography (eluted with 60% EtOAc in hexane) to afford 16.7 mg (Y: 98.8%) of desired compound Ia; $^1$H-NMR ($CDCl_3$, 300 MHz) δ ppm: 8.14 (d, J=8.7 Hz, 2H), 7.73 (d, J=8.7 Hz, 2H), 7.71–7.24 (m, 11H), 7.00 (d, exch, J=9.0 Hz, 1H), 6.18 (m, 2H), 6.04 (dd, $J_1$=9.9 Hz, $J_2$=5.6 Hz, 1H), 5.86–5.76 (m, 3H), 5.07 (d, J=5.6 Hz 1H), 4.75 (m, 1H), 4.35 (AB q, J=8.2 Hz, 2H), 3.97 (d, J=6.4 Hz, 1H), 3.53 (d, J=4.8 Hz, 1H), 2.37–1.12 (m, 21H, including s at 1.36, 3H; 2.21, 3H; 1.85, 3H; 1.71, 3H; 1.22, 3H; 1.13, 3H); $^{13}$C-NMR ($CDCl_3$, 75 MHz): δ ppm: 205.3, 172.5, 169.7, 169.6, 167.9, 141.1, 139.9, 138.0, 133.9, 133.8, 133.7, 132.0, 130.2, 129.2, 129.0, 128.7, 2, 128.7, 128.3, 127.0, 126.9, 126.3, 81.2, 78.6, 77.2, 76.4, 75.8, 75.5, 73.2, 72.2, 55.5, 54.8, 43.0, 41.6, 35.9, 26.4, 22.7, 21.6, 20.8, 20.3, 14.6; MS (FAB): 836 (MH).

EXAMPLE 4

6,7-dehydrobaccatin III (VIa)

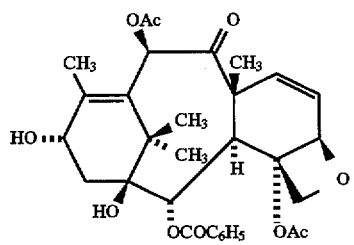

A solution of 6,7-dehydropaclitaxel (1.13 g, 1.35 mmol) in dichloromethane/2% methanol (60 mL) was treated with tetrabutylammonium borohydride (694 mg, 2.70 mmol) and the resulting solution was allowed to be stirred at ambient temperature for 5 h. The reaction was quenched by addition of saturated aqueous ammonium chloride (10 mL) and the organic fraction was dried ($MgSO_4$) and concentrated. The crude product was chromatographed on silica gel (eluted with 10% ethyl acetate in hexanes) to furnish a white solid which was then recrystallized from methanol (630 mg, Y: 82%); m.p. 224–°230° C. (dec.); $^1$H-NMR (300 MHz, $CDCl_3$): δ 8.15–8.09 (m, 2H), 7.64–7.58 (m, 1H), 7.51–7.45 (m, 2H), 6.46 (s, 1H), 6.05 (dd, 1H, J=6.0, 9.0 Hz), 5.86 (d, 1H, 12.0 Hz), 5.79 (d, 1H, J=6.0 Hz), 5.11 (d, 1H, J=6.0 Hz), 4.89–4.82 (m, 1H), 4.35 (ABq, 2H, J=6.0, 36.0 Hz), 4.09 (d, 1H, J=6.0 Hz), 2.35–2.18 (m, 10H, including singlets at 2.26, 2.21), 2.01 (s, 3H), 1.83 (s, 3H), 1.10–1.07 (m, 6H); $^{13}$C-NMR (75.6 MHz, $CDCl_3$): δ 205.4, 170.2, 169.5, 166.8, 145.3, 139.7, 133.5, 132.4, 129.9, 129.2, 128.5, 126.1, 81.1, 80.9, 78.9, 78.6, 76.3, 76.2, 75.3, 67.7, 55.4, 44.1, 42.5, 41.6, 38.9, 26.2., 22.6, 20.9, 20.7, 20.1, 14.8, 14.5.

EXAMPLE 5

6,7-dehydro-2'-O-triethylsilyl-3'-(2-furyl)-3'-N-debenzoyl-N-t-butoxycarbonylpaclitaxel (VIIIa)

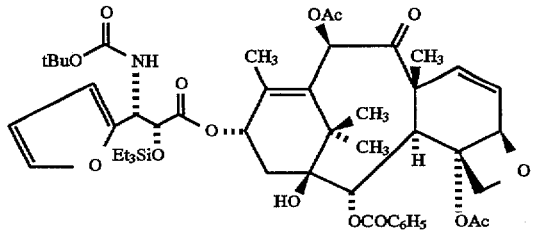

A solution of 6,7-dehydrobaccatin III (42 mg, 0.074 mmol) in dry tetrahydrofuran (5 mL) was flushed with an inert atmosphere and cooled to –55° C. in a dry ice/acetone bath. To this solution was added lithium-hexamethyldisilazane (0.5M solution in THF, 0.24 mL, 0.8 mmol) dropwise via syringe. The resulting pale yellow solution was allowed to be stirred for 5 min, then a tetrahydrofuran (2 mL) solution of racemic N-t-butoxycarbonyl-4-(2-furyl)-azetidinone (VIIa) (130.8 mg, 0.35 mmol) was added over a 5 min period. The cooling bath was then replaced with an ice/brine bath and the resulting solution allowed to be stirred at 0° C. for a 1 h period. The reaction was quenched by addition of saturated NH$_4$Cl solution (2 mL) then was diluted with ethyl acetate (25 mL) and washed with water (2×10 mL). The organic fraction was dried (MgSO$_4$) and concentrated to give the desired product as a crude colorless oil. The crude product was purified on silica gel using hexanes/ethyl acetate (7:3) as eluant. This process furnished the desired product as a colorless glass (59.5 mg, Y: 86%); $^1$H-NMR (300 MHz, CDCl$_3$): δ 8.14 (d, 2H, J=9.0 Hz), 7.60–7.37 (m, 3H), 6.35–6.33 (m, 1H), 6.24–6.20 (m, 3H), 6.06 (dd, 1H, J=6.0, 9.0 Hz), 5.87–5.84 (m, 2H), 5.30 (d, 2H, J=6.0 Hz), 5.11 (d, 1H, J=3.0 Hz), 4.75 (s, 1H), 4.36 (ABq, 2H, J=6.0, 39.0 Hz), 4.04 (d, 1H, J=6.0 Hz), 2.47 (s, 3H), 2.45–2.25 (m, 2H), 2.22 (s, 3H), 1.90–1.14 (m, 23H, including singlets at 1.86, 1.82, 1.34, 1.25, 1.14), 0.87–0.73 (m, 9H), 0.55–0.37 (m, 6H); $^{13}$C-NMR (75.6 MHz, CDCl$_3$): δ 2.5.5, 171.1, 169.5, 166.9, 155.3, 152.0, 142.0, 141.8, 139.9, 133.6, 133.4, 130.1, 129.1, 128.6, 126.1, 110.6, 107.2, 81.2, 80.9, 80.1, 78.6, 76.5, 76.3, 75.9, 75.6, 72.3, 71.9, 55.4, 52.7, 43.0, 41.3, 35.6, 28.1, 26.0, 22.8, 21.9, 20.7, 20.3, 14.5, 6.4, 4.2.

EXAMPLE 6

6,7-Dehydro-3'-(2-furyl)-3'-N-debenzoyl-N-t-butoxycarbonylpaclitaxel (Ib)

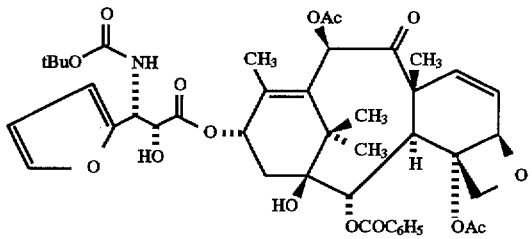

A solution of 2'-O-sityl protected substrate VIIIa (59.5 mg, 0.063 mmol) in acetonitrile (2 mL) was cooled to 0° C. in an ice/brine bath. To this solution was added 1 N HCl (0.5 mL, 6 eq.) and the reaction was allowed to stir for 1 h at that temperature. The solvent was then evaporated under vacuum and the residue was partitioned between ethyl acetate (25 mL) and water (10 mL). The organic fraction was dried (MgSO$_4$) and concentrated to give a white foam. The crude product was purified on silica gel using 10% CH$_3$CN in CH$_2$Cl$_2$ as eluant. The desired product was isolated as a white foam (46 mg, Y: 88%); $^1$H-NMR (300 MHz, CDCl$_3$): δ 8.14 (d, 2H, J=6.0 Hz), 7.62–7.46 (m, 3H), 6.37–6.30 (m, 2H), 6.31–6.20 (in, 2H), 6.06 (dd, 1H, J=6.0, 12.0 Hz), 5.87–5.83 (m, 2H), 5–35–5.23 (m, 2H), 5.10 (d, 1H, J=6.0 Hz), 4.70 (s, 1H), 4.37 (ABq, 2H, J=9.0, 42.0 Hz), 4.02 (d, 1H, J=6.0 Hz), 3.31 (bs, 1H), 2.40–1.15 (m, 31H, including singlets at 2.40, 2.23, 1.85, 1.79, 1.35, 1.25, 1.15); $^{13}$C-NMR (75.6 MHz, CDCl$_3$): δ 205.2, 169.4, 166.9, 142.3, 141.3, 139.7, 133.5, 130.0, 129.0, 128.5, 126.1, 110.5, 107.2, 81.1, 80.9, 78.5, 76.2, 75.7, 75.4, 72.2, 71.6, 55.3, 51.5, 42.9, 41.4, 35.5, 28.0, 26.0, 2.5, 21.6, 20.6, 20.1, 14.4; HRMS Calcd for MH$^+$ C$_{43}$H$_{52}$NO$_{15}$: 822.3337; Found: 822.3364

EXAMPLE 7

6,7-Dehydro-3'-(2-furyl) paclitaxel (Ic)

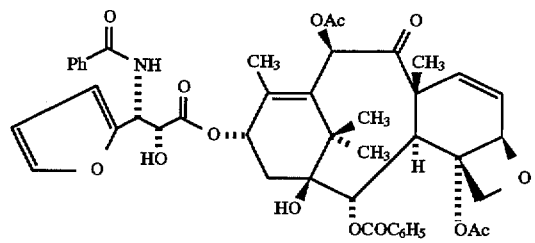

A solution of 6,7-dehydrobaccatin III (VIa)(191.4 mg, 0.33 mmol) in dry tetrahydrofuran (5mL) was flushed with an inert atmosphere and cooled to −55° C. in a dry ice/acetone bath. To this solution was added lithium hexamethyldisilazane (1M solution in hexane, 0.4 mL, 0.4 mmol) dropwise via syringe. The resulting pale yellow solution was allowed to stir for 5 min, then a tetrahydrofuran (2 mL) solution of the (3R, 4S)-N-benzoyl-4-(2-furyl)azetidinone (VIIa')(150.0 mg, 0.4 mmol) was added over a 5 min period. The cooling bath was then replaced with an ice/brine bath and the resulting solution allowed to stir at 0° C. for a 1 h period. The reaction was quenched by addition of saturated NH$_4$Cl solution (2 mL) then was diluted with ethyl acetate (25 mL) and washed with water (2×10 mL). The organic fraction was dried (MgSO$_4$) and concentrated to give 6,7-dehydro-2'-O-triethylsilyl-3'-(2-furyl)paclitaxel as a crude colorless oil.

A solution of the crude 6,7-dehydro-2'-O-triethylsilyl-3'-(2-furyl) paclitaxel (189 mg) in acetonitrile (2 mL) was cooled to 0° C. in an ice/brine bath. To this solution was added 1N HCl (0.5 mL) and the reaction was allowed to stir for 1 h at that temperature. The solvent was then evaporated under vacuum and the residue was partitioned between ethyl acetate (25 mL) and water (10 mL). The organic fraction was dried (MgSO$_4$) and concentrated to give a white foam. The crude product was purified on silica gel using 20% CH$_3$CN in CH$_2$Cl$_2$ as eluant. The title product was isolated as a white foam (140 mg, Y: 51%); $^1$H-NMR (300 MHz, CDCl$_3$) δ 8.15 (d, 2H, J=9.0 Hz), 7.73 (d, 2H, J=9.0 Hz), 7.61–7.37 (m, 6H), 6.92 (d, 1H, J=9.0 Hz), 6.38 (d, 2H, J=1.3 Hz), 6.21 (s, 2H), 6.06 (dd, 1H, J=6.0, 9.0 Hz), 5.89–5.84 (m, 2H), 5.10 (d, 1H, J=6.0 Hz), 4.80 (dd, 1H, J=3.0, 6.0 Hz), 4.36 (ABq, 2H, J=9.0, 36.0 Hz), 4.01 (d, 1H, J=6.0 Hz), 3.58 (d, 1H, J=6.0 Hz), 2.43–1.74 (m, 17H, including singlets at 2.42, 2.22, 1.99, 1.86, 1.76), 1.23–1.10 (m, 6H, including singlets at 1.23, 1.14); $^{13}$C-NMR (75.6 MHz, CDCl$_3$) δ 205.1, 172.0, 169.6, 169.4, 166.9, 166.8, 150.7, 142.5, 141.0, 139.7, 133.8, 133.6, 133.2, 131.9, 130.0, 129.1, 128.5, 126.9, 126.1, 110.6, 107.8, 81.1, 81.0, 78.4, 76.3, 75.7, 75.4, 72.1, 71.5, 55.3, 50.0, 42.9, 41.5, 35.7, 26.9, 26.2, 22.5, 21.5, 20.6, 20.2, 14.4.

EXAMPLE 8

6,7-dehydro-2'-O-triethylsilyl-3'-(2-thienyl)-3'-N-debenzoyl-N-t-butoxycarbonylpaclitaxel (VIIIb)

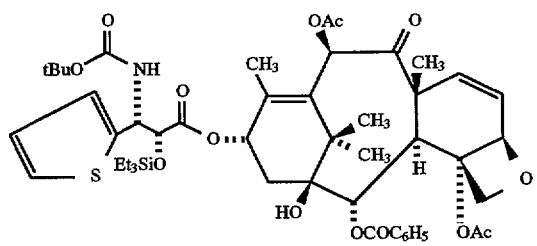

The title compound was prepared in the similar manner as compound VIIIa in Example 5; $^1$H-NMR (300 MHz, CDCl$_3$) δ 8.14 (d, 2H, J=9.0 Hz), 7.63–7.58 (m, 1H), 7.49 (t, 2H, J=9.0 Hz), 7.26–7.23 (m, 1H), 6.99–6.93 (m, 2H), 6.23–6.19 (m, 2H), 6.06 (dd, 1H, J=3.0, 9.0 Hz), 5.87–5.84 (m, 2H), 5.52–5.40 (m, 2H), 5.10 (d, H, J=6.0 Hz), 4.55 (d, 1H, J=1.8 Hz), 4.38 (ABq, 2H, J=9.0, 42.0 Hz), 4.03 (d, 1H, J=6.0 Hz), 2.47–2.20 (m, 8H, including singlets at 2.42, 2.22), 1.88–173 (m, 7H, including singlets at 1.86, 1.81), 1.43–1.14 (m, 15 H, including singlets at 1.32, 1.26, 1.14), 0.90–0.81 (m, 9H), 0.59–0.42 (m, 6H); $^{13}$C-NMR (75.6 MHz, CDCl$_3$): δ 205.4, 171.0, 169.5, 169.2, 166.9, 141.9, 139.9, 133.6, 133.4, 130.1, 129.1, 128.6, 126.8, 126.1, 124.6, 124.5, 81.2, 81.0, 80.1, 78.7, 76.2, 75.8, 75.7, 75.2, 71.2, 55.3, 53.7, 43.0, 41.3, 35.7, 28.1, 26.1, 22.9, 22.0, 20.7, 20.4, 14.5, 6.5, 4.4.

EXAMPLE 9

6,7-Dehydro-3'-2-thienyl)-3'-N-debenzoyl-N-t-butoxycarbonylpaclitaxel (Id)

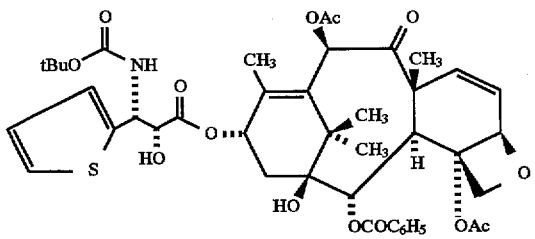

The title compound was obtained in a similar manner as compound Ib in Example 6; $^1$H-NMR (300 MHz, CDCl$_3$) δ 8.13 (d, 2H, J=6.0 Hz), 7.63–7.58 (m, 1H), 7.49 (t, 2H, J=6.0 Hz), 7.26–7.24 (m, 1H), 7.06 (d, 1H, J=6.0 Hz), 6.99–6.96 (m, 1H), 6.22–6.19 (m, 2H), 6.04 (dd, 1H, J=3.0, 10.0 Hz), 5.86–5.81 (m, 2H), 5.47–5.37 (m, 2H), 5.08 (d, 1H, J=6.0 Hz), 4.61 (dd, 1H, J=2.1, 5.4 Hz), 4.35 (ABq, 2H, J=8.1, 39.0 Hz), 4.00 (d, 1H, J=6.0 Hz), 3.56–3.53 (m, 1H), 2.37–2.20 (m, 8 H, including singlets at 2.37, 2.22), 1.98–1.72 (m, 7H, including singlets at 1.96, 1.86, 1.75), 1.39–1.14 (m, 15H, including singlets at 1.33, 1.24, 1.14); $^{13}$C-NMR (75.6 MHz, CDCl$_3$) δ 205.2, 169.5, 169.4, 166.9, 154.9, 141.3, 139.8, 133.7, 133.6, 133.5, 130.1, 129.9, 129.1, 128.6, 126.9, 126.2, 125.3, 125.2, 81.1, 81.0, 80.3, 78.5, 76.3, 75.8, 75.5, 73.3, 72.3, 55.4, 52.7, 43.0, 41.5, 35.6, 28.1, 26.2, 22.6, 21.6, 20.7, 20.2, 14.4.

EXAMPLE 10

Preparation of hydrobenzamide, PhCH(—N═CHPh)$_2$

To a 3 L 3-necked flask equipped with a mechanical stirrer and a thermometer was added 1 L of concentrated NOH (ca 30%) (14.8 moles). A solution of benzaldehyde (265 g, 2.50 mol) in 500 mL of 2-propanol was added in one portion. The mixture was stirred vigorously at ca 22° C. for 43 hours. The resulting slurry was filtered and the filter cake was washed with water (1 L). After drying in vacuo, 242.4 g of hydrobenzamide was obtained as a white solid (mp 100°–102° C.) for a 97.4% yield.

The above procedure can be followed to prepare bis-imines of the general formula R$^2$CH(—N═CHR$^2$)$_2$: i.e. hydrofuramide (R$^2$=2-furyl) hydrothienamide (R$^2$=2-thienyl)

EXAMPLE 11

(±)-cis-3-Acetyloxy-1-[phenyl)(benzylidenimino)methyl]-4-phenylazetidin-2-one (XIVa)

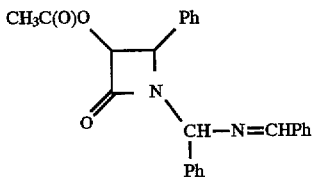

To a 1 L, 3-necked round bottom flask equipped with a thermometer, magnetic stirrer and dropping funnel was added hydrobenzamide (30.00 g, 100.5 mmol) and ethyl acetate (150 mL). With stirring and under a blanket of argon, the reaction mixture was cooled to 5° C. and triethylamine (16.8 mL, 121 mmol) was added. A solution of acetoxy-acetyl chloride (12.4 mL, 116 mmol) in ethyl acetate (300 mL) was then added dropwise over a 90 min period. After 16 h at this temperature, the reaction mixture was allowed to warm to 20° C. (1.5 h) and transferred to a separatory funnel. The organic layer was washed successively with aqueous NH$_4$Cl (sat) (150 mL, 100 mL), aqueous NaHCO$_3$ (saturated) (120 mL) and brine (120 mL). For purposes of characterization, the title compound can be isolated at this stage by drying the organic phase over MgSO$_4$, filtering, and removing the solvent in vacuo. This provided the desired product in quantitative crude yield as a red glass.

HPLC purity (area): 87.9% (1:1 mixture of diastereomers); $^1$H-NMR (CDCl$_3$, 200 MHz): δ 8.45 (s, 1H, N═CH), 7.80–7.85 (m, 1H, Ph), 7.60–7.65 (m, 1H, Ph), 7.26–7.50 (m, 9H, Ph), 7.00–7.10 (m, 4H, Ph), 6.28 (s, 0.5H, NCHN), 6.23 (s, 0.5H, NCHN), 5.81 (d, J=4.8 Hz, 0.5 H, H-3), 5.76 (d, J=4.8 Hz, 0.5H, H-3), 5.30 (d, J=4.8 Hz, 0.5 H, H-4), 4.75 (d, J=4.8 Hz, 0.5 H, H-4), 1.63 (s, 3H, CH$_3$CO); IR (KBr): ν(cm$^{-1}$)=1763 (C═O), 1641 (C═N); UV (methanol): λ max (nm)=216, 252.

EXAMPLE 12

(±)-cis-3-Acetyloxy-4-phenylazetidin-2-one (XVa)

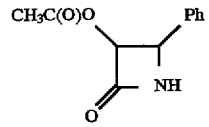

The solution of the compound of Example 11 in ethyl acetate (500 mL) from above was carefully transferred, under a stream of argon, to a 2.0 L Parr flask containing 10% palladium on activated charcoal (6.00 g). This mixture was treated with hydrogen (4 atm) for 20 h whereupon the catalyst was removed by filtration through a pad of Celite. The filter cake was slurried in ethyl acetate (200 mL), stirred (10 min) and filtered. The filter cake was rinsed with ethyl acetate (100 mL) and the filtrates combined. The organic layer was washed with 10% HCl (300 mL) and both layers filtered through a sintered glass funnel to remove the white precipitate (dibenzylamine.HCl) which was rinsed with ethyl acetate (100 mL). The phases were separated and the organic layer was washed with another portion of 10% HCl (200 mL). The combined 10% HCl washes were re-extracted with ethyl acetate (200 mL) and the combined organic layers were washed with aqueous $NaHCO_3$ (saturated) (300 mL) and brine (250 mL). The organic layer was dried over $MgSO_4$, filtered and concentrated in vacuo to a final volume of 75 mL. This mixture was cooled to 4° C. and the precipitated product isolated by filtration. The filter cake was washed with hexane (200 mL) to provide 16.12 g (78.1% overall yield from hydrobenzamide) of the title compound as white needles. mp=150°–151° C.; HPLC purity (area): 99.8%; $^1$H-NMR ($CDCl_3$, 200 MHz): δ=7.30–7.38 (m, 5H, Ph), 6.54 (bs, exchangeable, 1H, NH), 5.87 (dd, J=2.7, 4.7 Hz, 1H, H-3), 5.04 (d, J=4.7 Hz, 1H, H-4), 1.67 (s, 3H, $CH_3CO$); IR (KBr): ν ($cm^{-1}$)=3210 (N-H), 1755, 1720 (C=O); KF: 0.17%.

Anal. Calcd. for $C_{11}H_{11}NO_3$: C, 64.38; H, 5.40; N, 6.83.

Found: C, 64.07; H, 5.34; N, 6.77.

EXAMPLE 13

(±)-cis-3-Acetyloxy-1-[(2-furyl) (2-furylmethylenimino)methyl]-4- 2-furyl)azetidin-2-one (XIVb)

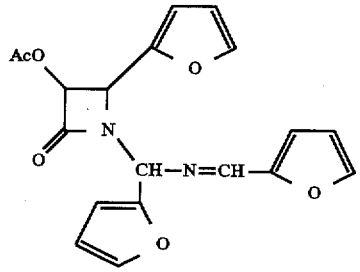

The title compound was prepared according to the procedure described in Example 11 except that hydrofuramide was used instead of hydrobenzamide and the reaction was performed on 18.6 mmol (vs 100 mmol) scale. Thus, hydrofuramide (5.00 g, 18.6 mmol), triethylamine (3.11 mL, 22.3 mmol) and acetoxyacetyl chloride (2.30 mL, 21.4 mmol) gave 6.192 g (Y: 90.4%) of the title compound as a pale red syrup. Obtained as a 1:1 mixture of diastereomers; $^1$H-NMR ($CDCl_3$; 200 MHz): δ 8.211 (s, 0.5H, N=CH), 8.208 (s, 0.5H, N=CH), 7.14–7.59 (m, 3H, furyl), 6.90 (d, J=3.5 Hz, 0.5H, furyl), 6.83 (d, J=3.5 Hz, 0.5H, furyl), 6.10–6.53 (m, 6H, furyl, NCHN), 5.90 (d, J=4.9 Hz, 0.5H, H-3), 5.86 (d, J=4.8 Hz, 0.5H, H-3), 5.35 (d, J=4.8 Hz, 0.5H, H-4), 4.90 (d, J=4.9 Hz, 0.5H, H-4), 1.91 (s, 1.5H, $CH_3CO$),1.88 (s, 1.5H, $CH_3CO$); IR (film): ν ($cm^{-1}$)=1778, 1753 (C=O), 1642 (C=N); UV (methanol): λ max (nm)=220, 278.

EXAMPLE 14

(±)-cis-3-(Acetyloxy)-4-(2-furyl)azetidin-2-one (XVb)

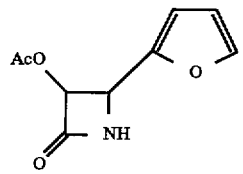

The title compound was prepared according to the procedure described in Example 12 except that the product was isolated by preparative TLC and the reaction was performed on the 2.7 mmol scale based on the original amount of hydrofuramide. Thus, the crude product of Example 13 (1.00 g) was re-dissolved in ethyl acetate (50 mL) and added to 10% palladium on activated charcoal (150 mg). Purification of the crude solid by preparative TLC (2 mm silica gel, eluted with 1:1 ethyl acetate/hexane) gave 386 mg (65.8% corrected overall yield from hydrofuramide) of the title compound as a yellow solid. This was recrystallized from ethyl acetate/hexane. mp=118°–119° C.; HPLC purity (area): 99.4%; $^1$H-NMR ($CDCl_3$, 200 MHz): δ 7.44 (t, J=1.3 Hz, 2H, furyl), 6.39 (d, J=1.3 Hz, 1H, furyl), 6.21 (bs, exchangeable, 1H, NH), 5.88 (dd, J=2.2, 4.6 Hz, 1H, H-3), 5.05 (d, J=4.6 Hz, 1H, H-4), 1.92 (s, 3H, $CH_3CO$); IR (KBr): ν ($cm^{-1}$)=3203 (N—H), 1756, 1726 (C=O); UV (methanol): λ max (nm)=222.

EXAMPLE 15

(±)-cis-3-Acetyloxy-1-[(2-thienyl) (2-thienylmethylenimino]methyl]-4-(2-thienyl) azetidin-2-one (XIVc)

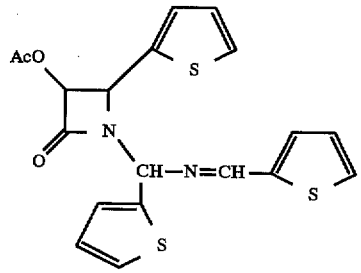

The title compound was prepared according to the procedure described in Example 11 except that hydrothienamide was used instead of hydrobenzamide. Thus, hydrothienamide (30 g, 94.7 mmol), thiethylamine (15.84 mL, 114 mmol) and acetoxyacetyl chloride (11.6 mL, 108 mmol) provided the title compound as viscous oil. The product obtained contained a mixture of diastereomers. $^1$H-NMR ($CDCl_3$): δ 8.52 (s, 1H), 8.502 (s, 1H), 7.51 (d, J=4.9 Hz, 1H), 7.45 (d, J=4.4 Hz, 1H), 7.41 (d, J=3.1 Hz, 1H), 7.37 (d, 1H), 7.30 (m, 3H), 7.16 (m, 1H), 7.16 (m, 3H), 7.09 (m, 2H), 6.94 (m, 1H), 6.89 (m, 1H), 6.81–6.74 (m, 4H), 6.48 (s, 1H), 6.43 (s, 1H), 5.85 (m, 2H), 5.59 (d, J=4.8 Hz, 1H), 5.17 (d, J=4.8 Hz, 1H), 1.87 (s, 3H), 1.86 (s, 3H).

EXAMPLE 16

(±)-cis-3-(Acetyloxy)-4-(2-thienyl)azetidin-2-one (XVc)

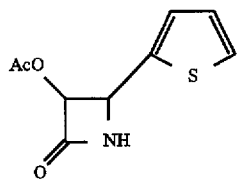

A 70% aqueous solution of acetic acid (0.35 mL glacial acetic acid and 0.15 mL water) was added in one portion to a stirred solution of compound XIVc (0.431 g, 1.03 mmol) in dichloromethane (2.93 ml) at 25° C. The reaction mixture was brought to reflux and stirred for 2.5 h. The reaction was diluted with 50 mL dichloromethane and then washed with two 75 mL portions of saturated aqueous sodium bicarbonate and then one 50 mL portion of saturated brine. The organic extract was concentrated in vacuo to a brown oil, dissolved in a minimal amount of dichtoromethane, and then placed on a silica gel column measuring 4" by 0.5". Elution using a gradient of 10 through 60% EtOAc in hexane provided less polar sideproducts and then the title compound (0.154 g, Y: 75%) as a white solid. $^1$H-NMR (CDCl$_3$): δ 7.32 (dd, J=4.7, 1.5 Hz, 1H), 7.03 (m, 2H), 6.75 (bs, 1H), 5.86 (dd, J=4.6, 2.7 Hz, 1H), 5.27 (d, J=5.3 Hz, 1H), 1.83 (s, 3H); $^{13}$C-NMR (CDCl$_3$): δ 169.3, 165.5, 138.4, 127.1, 127.07, 126.2, 78.3, 54.0, 20.0.

EXAMPLE 17

(±)-cis-3-Triethylsilyloxy-4-(2-furyl)-azetidin-2-one (XVIa)

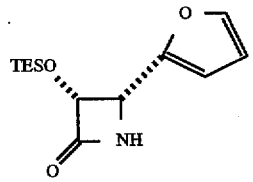

Acetoxy lactam XVb (3.78 g, 19.4 mmol) in 60 mL of methanol was stirred with K$_2$CO$_3$ (20 mg, 0.14 mmol) for 90 min and the solution neutralized with Dowex 50W-X8 and filtered. The filtrate was concentrated and the residue dissolved in 80 mL of anhydrous THF and stirred at 0° C. with imidazole (1.44 g, 21.2 mmol) and TESCl (triethylsilylchloride 3.4 mL, 20.2 mmol) for 30 min. The solution was diluted with ethyl acetate and washed with brine, dried over MgSO$_4$ and concentrated. The residue was chromatographed over silica gel (eluted with 3:1 hexane/ethyl acetate) to give 4.47g (Y: 86%) of the title compound as a colorless oil; IR(film) 3276 (broad), 1768, 1184, 732 cm$^{-1}$; $^1$H-NMR (CDCl$_3$, 300 MHz) δ 7.38 (s, 1H), 6.39 (bs, 1H), 6.35 (s, 2H), 5.05 (dd, J=4.6, 2.3 Hz, 1H), 4.78 (d, J=4.6 Hz, 1H), 0.82 (t, J=8.5 Hz, 6H), 0.50 (dq, J=8.5, 1.8 Hz, 9H); $^{13}$C-NMR (CDCl$_3$, 75.5 Hz) δ 169.6, 150.4, 142.6, 110.5, 109.1, 79.6, 53.2, 6.4, 4.4; FABMS (DCI) M+H calcd for C$_{13}$H$_{21}$NO$_3$Si: 268, Found: 268.

EXAMPLE 18

(±)-cis-3-Triethylsilyloxy-4-(2-furyl)-N-t-butoxycarbonylazetidin-2-one (VIIa)

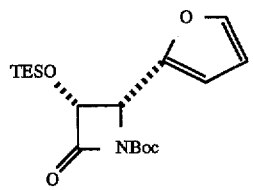

Azetidinone XVIa (2.05 g, 7.7 mmol) in 30 mL of dichloromethane was stirred at 0° C. with diisopropylethyl amine (1.5 mL, 8.6 mmol) and di-t-butylcarbonate (2.0 g, 9.2 mmol) in addition to a catalytic amount of dimethylaminopyridine (DMAP). The solution was diluted with dichloromethane and washed with brine, dried over MgSO$_4$ and concentrated. The residue was chromatographed over silica gel (eluted with 8:1 hexane/ethyl acetate) to give 2.0 (Y: 70%) of the title compound as a waxy solid; IR(KBr) 1822, 1806, 1712, 1370, 1348, 1016 cm$^{-1}$; $^1$H-NMR (CDCl$_3$, 300 MHz) δ 7.38 (m, 1H), 6.34 (m, 2H), 5.04 (ABq, J=12.4, 5.5 Hz, 2H), 1.39 (s, 9H), 0.82 (t, 9H), 0.50 (m, 6H); $^{13}$C-NMR (CDCl$_3$, 75.5 Hz) δ 165.7, 148.0, 147.7, 142.8, 110.5, 109.7, 83.4, 77.4, 56.0, 27.8, 6.3, 4.4; DCIMS M+H calcd for C$_{18}$H$_{29}$NO$_5$Si: 368, Found: 368.

EXAMPLE 19

(±)-cis-3-Triethylsilyloxy-4-(2-thienyl)-azetidin-2-one (XVIb)

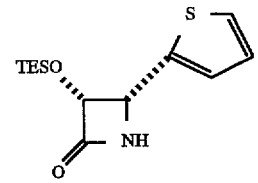

A solution of 3-acetoxy lactam XVc (2.5 g, 11.8 mmol) was dissolved in methanol (10 mL) and treated with saturated aqueous sodium bicarbonate (10 mL) and the resulting slurry was allowed to stir at ambient temperature for 3 h. The reaction was then diluted with ethyl acetate (20 mL) and washed with water (15 mL). The aqueous fraction was back extracted several times with ethyl acetate and the combined organic fractions were dried (MgSO$_4$) and concentrated to give a yellow solid (Y: 1.7 g). The crude material was dissolved in dry tetrahydrofuran (20 mL) and the solution was cooled to 5° C. in an ice/water bath. Imidazole (752 mg, 1.1 eq) was then added. After stirring 5 min, triethylchlorosilane (1.85 mL, 1.1 eq) was added dropwise. The resulting suspension was allowed to stir for 3 h at that temperature; then the solids were removed by filtration. The organic fraction was washed with water (2×20 mL) then dried (MgSO$_4$) and concentrated. The crude product was purified by silica gel column chromatography (eluted with hexanes/ethyl acetate 7:3) to give the desired product as a colorless solid (1.5 g, Y: 45%). m.p. 70°–71° C.; $^1$H-NMR (300 MHz, CDCl$_3$): δ 7.32–7.30 (m, 1H); 7.05–6.98 (m, 2H), 5.06–5.05 (m, 2H), 0.82 (t, 9H, J=8 Hz) , 0.55–0.46 (m, 6H); $^{13}$C-NMR (75.6 MHz, CDCl$_3$): δ 169.1, 139.7, 126.5, 126.4, 125.8, 79.4, 55.1, 6.3, 4.4.

Alternate Run:

Acetoxy lactam XVc (2.0 g, 9.37 mmol) in 40 mL of methanol was stirred with $K_2CO_3$ (60 mg, 0.43 mmol) for 30 min and the solution neutralized with Dowex 50W-X8 and filtered. The filtrate was concentrated and the residue dissolved in 50 mL of anhydrous THF and stirred at 0° C. with imidazole (0.85 g, 11.3 mmol) and TESCl (1.9 mL, 12.5 mmol) for 30 min. The solution was diluted with ethyl acetate and washed with brine, dried over $MgSO_4$ and concentrated. The residue was chromatographed over silica gel (eluted with 3:1 hexane/ethyl acetate) to give 2.13 g (Y: 86%) of the title product as a colorless oil.

EXAMPLE 20

(±)-cis-3-Triethylsilyloxy-4-(2-thienyl)-N-t-butoxycarbonylazetidin-2-one (VIIb)

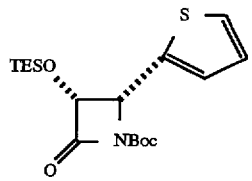

A solution of the silyl azetidinone XVIb (425.7 mg, 1.48 mmol) was dissolved in dichloromethane (10 mL) and cooled to 5° C. in an ice/water bath. The reaction was treated with a catalytic amount of DMAP followed by TESCl (0.25 mL, 1.0 eq) then by di-t-butylcarbonate (388.4 mg, 1.2 eq). After stirring 2 h at that temperature the reaction was quenched with saturated aqueous sodium bicarbonate (5 mL) and the organic fraction was washed with water (5 mL) then dried ($MgSO_4$), passed through a short plug of silica gel and concentrated to give the desired product as a colorless oil (525.3 mg, Y: 93%); $^1$H-NMR (300 MHz, $CDCl_3$): δ 7.31–7.29 (m, 1H), 7.08–7.07 (m 1H), 7.00–6.58 (m, 1H), 5.31 (d, 1H, J=6 Hz), 5.03 (d, 1H, J=6 Hz), 1.40 (s, 9H), 0.83 (t, 9H, J=8 Hz), 0.56–0.47 (m, 6H); $^{13}$C-NMR (75.6 MHz, $CDCl_3$): 165.5, 147.5, 136.4, 127.6, 126.2, 126.1, 83.3, 77.3, 57.9, 27.7, 6.2, 4.3.

EXAMPLE 21

Representative example to derivatize, selectively, the C-10 position of 10-desacetylbaccatin III 10-Benzoyl-10-desacetyl-7-triethylsilylbaccatin III ($X^1$a)

Under argon atmosphere, the baccatin derivate of formula IX in which equals $SiEt_3$ (43.5 mg, 0.066 mmol) was dissolved in dry tetrahydrofuran (1.0 mL). The solution was cooled to −40° C. and n-BuLi (0.050 mL, 0.82 mmol, 1.6M solution) was added slowly. After 5 minutes of stirring, benzoyl chloride (0.030 mL, 0.26 mmol) was added and the reaction mixture was warmed to 0° C. The reaction mixture was stirred for 1.5 h before quenching into a saturated solution of ammonium chloride (2 mL). The aqueous medium was extracted with ethyl acetate (2×5 mL), dried (magnesium sulfate), and evaporated to afford an oil. Flash silica gel chromatography (eluted with 50% ethyl acetate in hexanes) afford the title compound (30 mg, Y: 60%, a compound of formula $X^i$ in which $R^4$=Si(Et)$_3$, $R'''$=OCOC$_6$H$_5$) as a foam; $^1$H-NMR ($CDCl_3$): δ 8.17–8.05 (m, 4H), 7.64–7.42 (m, 6H), 6.67 (s, 1H), 5.67 (d, 1H), 4.95 (d, 1H), 4.81 (m, 1H), 4.56 (dd, 1H), 4.30 (d, 1H), 4.14 (d, 1H), 3.92 (d, 1H), 2.50 (In, 1H), 2.30–2.0 (m, 18H), 1.92–1.80 (m, 1H), 1.72–1.62 (bs, 4H), 1.30 (s, 3H), 1.00 (s, 3H), 0.89 (t,3H), 0.56 (q, 6H); HRMS (FAB/NOBA): Calculated for $C_{42}H_{54}O_{11}Si$ (MH$^+$): 762.3435. Found 762.3427.

Using this methodology, C-10 carbonates, sulfonates, carbamates, ethers, etc., can be prepared. Yields will be found better when lithium hexamethyldisilazane is employed.

EXAMPLE 22

2'-O-Benzyloxycarbonyl-6α-hydroxy-7α-hydroxypaclitaxel (XIIa)

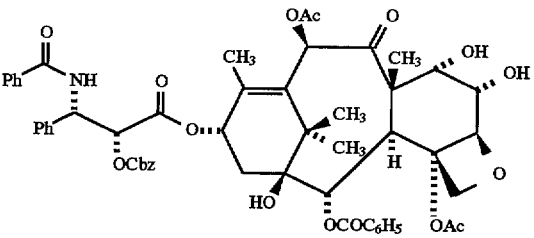

A solution of 2'-O-benzyloxycarbonyl-6,7-dehydropaclitaxel (100 mg, 0.1 mmol) in dry tetrahydrofuran (3 mL) was cooled to 5° C. in an ice/water bath. The solution was treated with pyridine (24 μL, 0.3 mmol) and 4-methylmorpholine-N-oxide (12 mg, 0.1 mmol). After complete solution was attained, a catalytic amount of osmium tetroxide (2.5 mg, 0.01 mmol) was added and the resulting yellow solution was placed in the refrigerator for 96 h. The resulting solution was diluted with ethyl acetate (10 mL) and washed with saturated odium bicarbonate (5 mL) then water (10 mL). The organic fraction was dried ($MgSO_4$) and concentrated to give the crude product as a colorless foam. The product was purified by chromatography on silica gel (eluted with 20% $CH_3CN$ in $CH_2Cl_2$) to furnish the desired product as a white foam (47 mg, Y: 47%); $^1$H-NMR ($CDCl_3$, 300 MHz): δ 8.12 (d, 2H, J=6.0 Hz), 7.68 (d, 2H, J=6.0 Hz), 7.60–7.29 (m, (m, 16H), 6.93 (d, 1H, J=9.0 Hz), 6.80 (s, 1H), 6.24 (t, 1H, J=9.0 Hz), 5.99 (dd, 1H, J=3.0, 9.0 Hz), 5.71 (d, 1H, J=6.0 Hz), 5.45 (d, 1H, J=3.0 Hz), 5.27–5.13 (m, 2H), 4.67–4.63 (m, 2H), 4.33 (s, 2H), 4.16–4.12 (m, 1H), 3.85 (d, 1H, J=6.0 Hz), 3.65 (dd, 1H, J=3.0, 12.0 Hz), 2.87–2.84 (m, 1H), 2.52 (s, 3H), 2.42–2.33 (m, 1H), 2.20–2.12 (m, 4H), 2.01 (s, 1H), 1.89 (s, 3H), 1.61 (s, 3H), 1.16 (s, 3H), 1.11 (s, $^{13}$C-NMR ($CDCl_3$, 75.6 MHz): δ 205.9, 172.3, 169.3, 167.6, 167.1, 166.9, 154.0, 140.5, 136.6, 134.2, 133.7, 133.4, 132.9, 132.0, 130.2, 129.1, 128.9, 128.8, 128.7, 128.6, 128.5, 128.4, 127.1, 126.4, 91.5, 84.1, 79.1, 77.9, 77.7, 77.6, 76.8, 76.6, 74.8, 72.0, 71.8, 70.7, 60.4, 57.6, 52.6, 42.6, 39.7, 36.0, 25.9, 22.5, 21.4, 21.0, 20.8, 15.4, 14.7, 14.1; HRMS calcd for $C_{55}H_{58}NO_{17}$: 1004.3705, found: 1004.3691.

EXAMPLE 23

6α-hydroxy-7α-hydroxypaclitaxel (Ie)

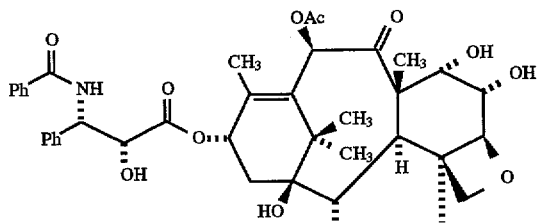

A solution of 2'-O-benzyloxycarbonyl-6α-hydroxy-7α-hydroxypaclitaxel (47 mg, 0.047 mmol) in ethyl acetate (3 mL) was placed in a Parr bottle and purged with argon. Palladium on carbon (20 mg) was added and the resulting suspension was shaken under 40 psi of hydrogen. After 3h the reaction was vented and the suspension was filtered through a short plug of Celite followed by concentration. The crude product was purified by silica gel chromatography (eluted with 20% $CH_3CN$ in $CH_2Cl_2$) to furnish the desired product as a white foam (20.2 mg, Y: 99% based on recovered starting material); $^1$H-NMR ($CDCl_3$, 300 Mz): δ 8.15 (dd, 2H, J=0.9, 8.0 Hz), 7.72 (dd, 2H, J=0.9, 9.0 Hz), 7.76–7.26 (m, 11H), 7.02 (d, 1H, J=9 Hz), 6.79 (s, 1H), 6.23 (t, 1H, J=9.0 Hz), 5.80 (dd, 1H, J=2.1, 8.7 Hz), 5.73 (d, 1H, J=7.2 Hz), 4.82–4.79 (m, 1H), 4.68–4.64 (m, 2H), 4.34 (s, 2H), 4.15 (apparent t, 1H, J=5.4 Hz), 3.85 (d, 1H, J=9.0 Hz), 3.69–3.60 (m, 2H), 2.83 (d, 1H, J=8.1 H z), 2.50 (s, 3H), 2.43–2.35 (m, 1H), 2.28–2.23 (m, 1H), 2.19 (s, 3H), 2.00 (s, 1H), 1.80 (s, 3H), 1.63 (s, 3H), 1.19 (s, 3H), 1.13 (s, 3H); $^3$C-NMR ($CDCl_3$, 75.6 MHz): δ 205.6, 172.6, 172.5, 139.9, 137.8, 133.6, 133.1, 131.8, 130.1, 128.9, 128.7, 128.5, 128.2, 126.9, 126.7, 91.4, 83.9, 78.9, 77.7, 77.5, 74.6, 73.0, 72.0, 71.8, 57.5, 54.7, 42.5, 39.5, 36.0, 25.9, 22.4, 21.1, 20.7, 15.2, 14.6.

EXAMPLE 24

Following the processes and Examples described in this application, the following specific paclitaxel derivatives of formula $I^2$ can be synthesized:

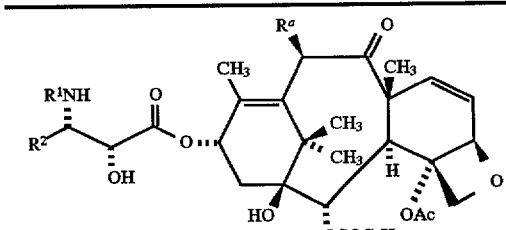

| Compound | $R^2$ | $R^1$ | $R^a$ |
|---|---|---|---|
| If | 2-furyl | $COC_6H_5$ | $OCH_3$ |
| Ig | 2-thienyl | $COC_6H_5$ | $OCH_3$ |
| Ih | 2-furyl | $COC_6H_5$ | $OSO_2CH_3$ |
| Ii | 2-thienyl | $COC_6H_5$ | $OSO_2CH_3$ |
| Ij | 2-furyl | $COC_6H_5$ | $OCOCH_2CH_2CH_3$ |
| Ik | 2-furyl | $COC_6H_5$ | $OSO_2$(4-methylphenyl) |
| Il | 2-thienyl | $COC_6H_5$ | $OSO_2$(4-bromophenyl) |
| Im | 2-furyl | $COC_6H_5$ | $OCO_2CH_2C_6H_5$ |
| In | 2-thienyl | $COC_6H_5$ | $OCO_2CH_2C_6H_5$ |
| Io | 2-furyl | $COC_6H_5$ | $OCOC_6H_5$ |
| Ip | 2-thienyl | $COC_6H_5$ | $OCOC_6H_5$ |
| Iq | 2-furyl | $CH_3CH(CH_3)CH_2OCO$ | OAc |
| Ir | 2-thienyl | $CH_3CH(CH_3)CH_2OCO$ | OAc |
| Is | phenyl | $CH_3CH(CH_3)CH_2OCO$ | OAc |
| It | 2-thienyl | $(CH_3)_2CHOCO$ | OAc |
| Iu | phenyl | $(CH_3)_2CHOCO$ | OAc |
| Iv | 2-furyl | $CH_2=CHCH_2OCO$ | OAc |
| Iw | 2-thienyl | $CH_2=CHCH_2OCO$ | OAc |
| Ix | phenyl | $CH_2=CHCH_2OCO$ | OAc |
| Iy | 2-furyl | cyclohexyl-OCO | OAc |
| Iz | 2-thienyl | cyclohexyl-OCO | OAc |
| Iaa | phenyl | cyclohexyl-OCO | OAc |
| Iab | 4-oxazolyl | $(CH_3)_2CHOCO$ | OAc |
| Iac | 2-methyl-4-oxzaolyl | $(CH_3)_2CHOCO$ | OAc |
| Iad | 4-oxazolyl | $(CH_3)_3COCO$ | OAc |
| Iae | 2-methyl-4-oxazolyl | $(CH_3)_3COCO$ | OAc |
| Iaf | 4-oxazolyl | $COC_6H_5$ | OAc |
| Iag | 2-methyl-4-oxazolyl | $COC_6H_5$ | OAc |
| Iah | 2-furyl | $(CH_3)_3COCO$ | $OCON(CH_3)_2$ |
| Iai | 2-thienyl | $(CH_3)_3COCO$ | $OCON(CH_3)_2$ |
| Iaj | 2-furyl | $COC_6H_5$ | $OCON(CH_3)_2$ |
| Iak | 2-thienyl | $COC_6H_5$ | $OCON(CH_3)_2$ |
| Ial | 4-oxazolyl | $(CH_3)_3COCO$ | $OCON(CH_3)_2$ |
| Iam | 2-methyl-4-oxazolyl | $(CH_3)_3COCO$ | $OCON(CH_3)_2$ |
| Ian | 4-oxazolyl | $COC_6H_5$ | $OCON(CH_3)_2$ |
| Iao | 2-methyl-4-oxazolyl | $COC_6H_5$ | $OCON(CH_3)_2$ |
| Iap | 2-thienyl | $COC_6H_5$ | $OCOCH_2CH_2CH_3$ |
| Iaq | phenyl | $(CH_3)_3COCO$ | $OCON(CH_3)_2$ |
| Iar | 2-thienyl | $COC_6H_5$ | $OCON(CH_3)_2$ |

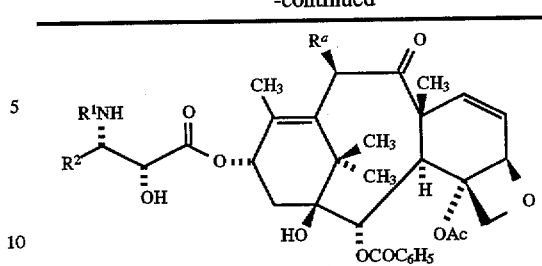

EXAMPLE 25

Following the processes and Examples described in this application, the following specific paclitaxel derivatives of formula $I^3$ can be synthesized:

| Compound | $R^2$ | $R^1$ | $R^a$ |
|---|---|---|---|
| Ias | 2-furyl | $COC_6H_5$ | $OCH_3$ |
| Iat | 2-thienyl | $COC_6H_5$ | $OCH_3$ |
| Iau | 2-furyl | $COC_6H_5$ | $OSO_2CH_3$ |

-continued

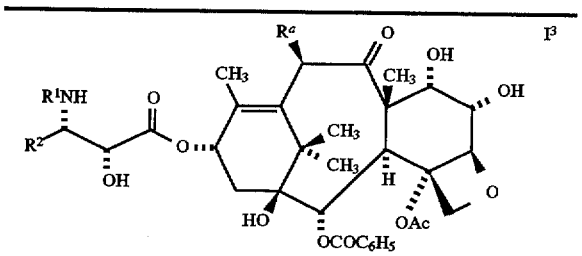

| Compound | R² | R¹ | Rᵃ |
|---|---|---|---|
| Iav | 2-thienyl | COC₆H₅ | OSO₂CH₃ |
| Iaw | 2-furyl | COC₆H₅ | OCOCH₂CH₂CH₃ |
| Iax | 2-furyl | COC₆H₅ | OSO₂(4-methylphenyl) |
| Iay | 2-thienyl | COC₆H₅ | OSO₂(4-bromophenyl) |
| Iaz | 2-furyl | COC₆H₅ | OCO₂CH₂C₆H₅ |
| Iba | 2-thienyl | COC₆H₅ | OCO₂CH₂C₆H₅ |
| Ibb | 2-furyl | COC₆H₅ | OCOC₆H₅ |
| Ibc | 2-thienyl | COC₆H₅ | OCOC₆H₅ |
| Ibd | 2-furyl | CH₃CH(CH₃)CH₂OCO | OAc |
| Ibe | 2-thienyl | CH₃CH(CH₃)CH₂OCO | OAc |
| Ibf | phenyl | CH₃CH(CH₃)CH₂OCO | OAc |
| Ibg | 2-thienyl | (CH₃)₂CHOCO | OAc |
| Ibh | phenyl | (CH₃)₂CHOCO | OAc |
| Ibi | 2-furyl | CH₂=CHCH₂OCO | OAc |
| Ibj | 2-thienyl | CH₂=CHCH₂OCO | OAc |
| Ibk | phenyl | CH₂=CHCH₂OCO | OAc |
| Ibl | 2-furyl | cyclohexyl-OCO | OAc |
| Ibm | 2-thienyl | cyclohexyl-OCO | OAc |
| Ibn | phenyl | cyclohexyl-OCO | OAc |
| Ibo | 4-oxazolyl | (CH₃)₂CHOCO | OAc |
| Ibp | 2-methyl-4-oxzaolyl | (CH₃)₂CHOCO | OAc |
| Ibq | 4-oxazolyl | (CH₃)₃COCO | OAc |
| Ibr | 2-methyl-4-oxazolyl | (CH₃)₃COCO | OAc |
| Ibs | 4-oxazolyl | COC₆H₅ | OAc |
| Ibt | 2-methyl-4-oxazolyl | COC₆H₅ | OAc |
| Ibu | 2-furyl | (CH₃)₃COCO | OCON(CH₃)₂ |
| Ibv | 2-thienyl | (CH₃)₃COCO | OCON(CH₃)₂ |
| Ibw | 2-furyl | COC₆H₅ | OCON(CH₃)₂ |
| Ibx | 2-thienyl | COC₆H₅ | OCON(CH₃)₂ |
| Iby | 4-oxazolyl | (CH₃)₃COCO | OCON(CH₃)₂ |
| Ibz | 2-methyl-4-oxazolyl | (CH₃)₃COCO | OCON(CH₃)₂ |
| Ica | 4-oxazolyl | COC₆H₅ | OCON(CH₃)₂ |
| Icb | 2-methyl-4-oxazolyl | COC₆H₅ | OCON(CH₃)₂ |
| Icc | 2-thienyl | COC₆H₅ | OCOCH₂CH₂CH₃ |
| Icd | phenyl | (CH₃)₃COCO | OCON(CH₃)₂ |
| Ice | 2-thienyl | COC₆H₅ | OCON(CH₃)₂ |

EXAMPLE 26

Biological Data
Mice M109 Model

Balb/c x DBA/2 $F_1$ hybrid mice were implanted intraperitoneally, as described by William Rose in *Evaluation of Madison 109 Lung Carcinoma as a Model for Screening Antitumor Drugs, Cancer Treatment Reports*, 65, No. 3–4 (1981), with 0.5 mL of a 2% (w/v) brei of M109 lung carcinoma.

Mice were treated with compound under study by receiving intraperitoneal injections of various doses on either days 1, 5 and 9 post-tumor implant or days 5 and 8 post-implant. Mice were followed daily for survival until approximately 75–90 days post-tumor implant. One group of mice per experiment remained untreated and served as the control group.

Median survival times of compound-treated (T) mice were compared to the median survial time of the control (C) mice. The ratio of the two values for each compound-treated group of mice was multiplied by 100 and expressed as a percentage (i.e. % T/C) in Table I for a representative compound.

TABLE I (IP M109 data)

| Compound | % T/C (dose in mg/kg/injection; schedule) |
|---|---|
| Ia | 161% (60 mg/kg/inj; d. 5 & 8) |

The compounds of the instant invention have tumor inhibiting activities in mammals. Thus, another aspect of the instant invention concerns with a method for inhibiting mammalian tumors sensitive to a compound of formula I.

The present invention also provides pharmaceutical formulations (compositions) containing a compound of formula I in combination with one or more pharmaceutically acceptable, inert or physiologically active, carriers, excipients, diluents or adjuvants. Examples of formulating paclitaxel or its related derivatives (including a possible dosage) are described in numerous literatures, for example in U.S. Pat. Nos. 4,960,790 and 4,814,470, and such examples may be followed to formulate the compounds of this invention. For example, the new compounds are administrable in the form of tablets, pills, powder mixtures, capsules, injectables, solutions, suppositories, emulsions, dispersions, food premix, and in other suitable forms. The pharmaceutical preparation which contains the compound is conveniently admixed with a nontoxic pharmaceutical organic carrier or a nontoxic pharmaceutical inorganic carrier, usually about 0.01 mg up to 2500 mg, or higher per dosage unit, preferably 50–500 mg. Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

The compounds of the invention can also be freeze dried and, if desired, combined with other pharmaceutically acceptable excipients to prepare formulations suitable for parenteral, injectable administration. For such administration, the formulation can be reconstituted in water (normal, saline), or a mixture of water and an organic solvent, such as propylene glycol, ethanol, and the like.

The compounds of present invention can be used as paclitaxel for treating mammalian tumors. The mode, dosage and schedule of administration of paclitaxel in human cancer patients have been extensively studied. See, for example *Ann. Int. Med.*, 111, pp 273–279 (1989). For the compounds of this invention, the dose to be administered, whether a single dose, multiple dose, or a daily dose, will of course vary with the particular compound employed because of the varying potency of the compound, the chosen route of administration, the size of the recipient and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. The dosage to be administered will be generally in the range of 0.8 to 8 mg/kg of body weight or about 50–275 mg/m$^2$ of the patient. An oncologist skilled in the art of cancer treatment will be able to ascertain, without undue experimentation, appropriate protocols for effective administration of the compounds of this present invention such a by referring to the earlier studies of paclitaxel and its derivatives.

We claim:

1. A compound of formula I

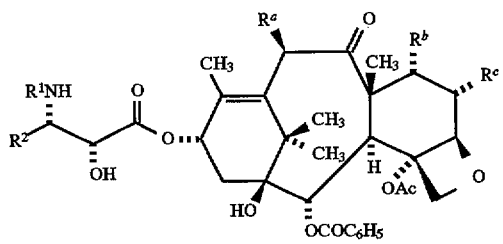

in which $R^1$ is —COR$^Z$ in which R$^Z$ is RO— or R;

$R^2$ is formula —W—R$^x$ in which W is a bond, $C_{2-6}$ alkenediyl, or —(CH$_2$)$_t$—, in which t is one to six; and R$^x$ is furylorthienyl optionally substituted with one to three same or different $C_{1-6}$ alkyl, $C_{1-6}$ alkoxy, halogen or —CF$_3$ groups;

R$^a$ is —OCOR, H, OH, —OR, —OSO$_2$R, —OCONR$^o$R, —OCONHR, —OCOO(CH$_2$)$_t$R or —OCOOR;

R$^b$ and R$^c$ are both hydroxy or together form a bond with the carbon atoms to which they are attached; and R and R$^o$ are independently $C_{1-6}$ alkyl, $C_{2-6}$ alkenyl, $C_{3-6}$ cycloalkyl, $C_{2-6}$ alkynyl, or phenyl optionally substituted with one to three same or different $C_{1-6}$ alkyl, $C_{1-6}$ alkoxy, halogen or —CF$_3$ groups.

2. A compound of claim 1 in which $R^1$ is benzoyl or t-butoxycarbonyl; $R^2$ is furyl or thienyl; R$^a$ is acetyloxy; and R$^b$ and R$^c$ together form a bond with the carbon atoms to which they are attached.

3. The compound of claim 2 that is 6,7-dehydro-3'-(2-furyl)-3'-N-debenzoyl-N-t-butoxycarbonylpaclitaxel.

4. The compound of claim 2 that is 6,7-dehydro-3'-(2-furyl)paclitaxel.

5. The compound of claim 2 that is 6,7-dehydro-3'-(2-thienyl)-3'-N- debenzoyl-N-t-butoxycarbonylpaclitaxel.

6. A compound of claim 1 in which $R^1$ is benzoyl or t-butoxycarbonyl; $R^2$ is furyl or thienyl; R$^a$ is acetyloxy; and R$^b$ and R$^c$ are hydroxy.

7. A pharmaceutical composition which comprises as an active ingredient a compound as claimed in any one of claims 1 to 6, or a pharmaceutically acceptable salt thereof, associated with one or more pharmaceutically acceptable carriers, excipients or diluents therefor.

* * * * *